(12) United States Patent
Spaulding

(10) Patent No.: US 9,805,166 B1
(45) Date of Patent: Oct. 31, 2017

(54) HOME HEALTHCARE MANAGEMENT SYSTEM AND HARDWARE AND SOFTWARE

(71) Applicant: Glenn Spaulding, Houston, TX (US)

(72) Inventor: Glenn Spaulding, Houston, TX (US)

(*) Notice: Subject to any disclaimer, the term of this patent is extended or adjusted under 35 U.S.C. 154(b) by 0 days.

(21) Appl. No.: 14/796,908

(22) Filed: Jul. 10, 2015

(51) Int. Cl.
*G06F 19/00* (2011.01)
*G06K 9/00* (2006.01)
*A61B 5/15* (2006.01)
*A61B 10/00* (2006.01)

(52) U.S. Cl.
CPC ............ *G06F 19/3418* (2013.01); *A61B 5/15* (2013.01); *G06F 19/321* (2013.01); *G06K 9/00134* (2013.01); *G06K 9/00147* (2013.01); *A61B 2010/0003* (2013.01); *A61B 2505/07* (2013.01)

(58) Field of Classification Search
None
See application file for complete search history.

(56) References Cited

FOREIGN PATENT DOCUMENTS

WO    WO 2016061563 A1 * 4/2016 ............. G02B 21/36

\* cited by examiner

*Primary Examiner* — Delomia L Gilliard

(57) ABSTRACT

A business method is described comprising doctorless testing, diagnosis, and treatment of patient diagnosed health maladies. Antithetical to the current regulatory and general public healthcare practices, in the doctorless method the patient has the equivalent of a clinical laboratory and physician's clinic at home. The herein disclosed microscope, blood tests, and physiological monitoring are patient selected, patient interpreted, and acted upon by the patient without physician support. The invention herein disclosed is a multi-element bundled comprehensive solution that lowers yearly primary healthcare costs to that of a cell phone, and will be purchased at retail stores such as Wal-Mart.

2 Claims, 15 Drawing Sheets

HOME HEALTHCARE MANAGEMENT SYSTEM AND HARDWARE AND SOFTWARE

CROSS-REFERENCE TO RELATED APPLICATIONS

This application claims the benefit of U.S. Provisional Application Ser. No. 61/472,193, filed on Mar. 5, 2011, entitled HOME HEALTHCARE MANAGEMENT SYSTEM AND HARDWARE, 61/430,973, filed on Jan. 8, 2011, entitled: HOME HEALTHCARE MANAGEMENT SYSTEM AND HARDWARE AND SOFTWARE, by inventor Glenn F. Spaulding, and U.S. Provisional Application Ser. No. 61/225,693, filed on Jul. 15, 2009, entitled: HOME HEALTHCARE MANAGEMENT SYSTEM AND HARDWARE, by inventor Glenn F. Spaulding. This application claims the benefit of U.S. application Ser. No. 12/835,386, filed on Jul. 13, 2010, entitled: HOME HEALTHCARE MANAGEMENT SYSTEM AND HARDWARE, by inventor Glenn F. Spaulding. This application claims the benefit of International Application No. PCT/US2010/041938, filed on Jul. 24, 2010, entitled: HOME HEALTHCARE MANAGEMENT SYSTEM AND HARDWARE, by inventor Glenn F. Spaulding, and application Ser. No. 13/440,459, filed on Apr. 5, 2012, by Glenn F. Spaulding—all the above fully incorporated herein.

STATEMENT REGARDING FEDERALLY SPONSORED RESEARCH OR DEVELOPMENT

Not Applicable.

REFERENCE TO A "MICROFICHE APPENDIX"

Not Applicable.

NOTICE OF MATERIAL SUBJECT TO COPYRIGHT PROTECTION

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates to a system for providing home healthcare management. More specifically, the present invention relates to a home healthcare system for providing home diagnoses, testing, and management of the information derived therefrom.

2. Description of the Related Art

Medical Diagnosis & Diagnostics

Throughout recorded time health care has increasingly relied upon trained healthcare personnel. This was in part due to the limited availability of education, and due to the limited access to medical knowledge bases. Prior to the general availability of the Internet, patients had to rely on limited medical resources.

Medical training includes four years of learning medical terminology and pathophysiological relationships, and many additional post-graduate training years to develop and understand the patient's contextual constructs for describing their disease, i.e., weighting factors and parsing important and tangential symptoms. Many have attempted to translate the complex pathophysiological relationships and interrelationships that they learned in medical school and through experience, into algorithms, branching trees, likelihood ratios, probabilities, tables and the like; sometimes referring to them as traditional medicine or evidence-based medicine. This is akin to behavior modeling of relationships which while adequate for predicting group behavior, falls short of predicting individual behaviors, needs and responses.

The translation of medical knowledge into a series of questions that can lead the patient into a diagnosis is cumbersome, impractical and fraught with error. By example, telephone answering services are a simplified implementation of this method. Press 1 for the following services, press 2 for the following services, etc., ostensibly guiding the listener to a final service. Often the listener is uncertain that the press 1 service is exactly what they are looking for, and may try another, ending up at an incorrect end-point. While on paper the flow and logic directing a listener to a particular service may seem clear, the listener does not have the advantage of context and will thus have a different interpretation of various words and may come to a different conclusion. Analogously, while a disease may have a common cause, the effects on the patient and how it is perceived is unique for every patient. Consequently, the current practice is to use health care professionals to map a patient's symptoms to current medical terminology and understanding and then recommend tests to drill down to the underlying cause, (e.g., iterative testings).

It is common for an illness as simple as a sore throat to take hours or days to evaluate. Time is spent 1) making an appointment; 2) adjusting the work schedule to accommodate the appointment; 3) driving to the appointment; 4) waiting to be seen; 5) testing; 6) waiting for the results from a distant laboratory; and 7) traveling back to work. And if test results are inconclusive, more tests are needed the next day. In other words the current health care model is comprised of: a health care provider who evaluates symptoms and selects the appropriate tests, support personnel that conduct the tests relaying the results back to the provider, and the provider determining if more tests are necessary. With rising health care costs, testing has become judicious as a cost cutting measure. Testing can be expensive because it includes the cost of the facilities to house the test and personnel, the cost of the instrument that conducts the tests, the government certification and compliant costs, the personnel costs to draw blood, personnel to maintain instruments, personnel to certify compliance, the cost of the test itself, and the administrative costs (e.g., computers, personnel, accounting, health care insurance, etc). As a result of Enterprise pressures to cut costs, patients are inadequately tested, and the patient's symptoms often are allowed to progress into more easily identified symptoms, i.e., they are diagnosed at a later time using less expensive means.

Enterprise systems (e.g., health maintenance organizations (HMOs), participating provider option (PPOs), Medicare and Medicaid, Public Health Care services, physician groups, etc.) are physician and business centric; most decisions stem from these two primaries. Physicians make diagnoses, recommend testing, and choose what will be entered into the patients history; business administrators review patients records, recommend tests, review photographs, and decide how widely the patient's records will be disseminated and what tests will be reimbursed. Patients have little or no control over the sharing and review of confidential information, who views the before and after photographs nor the extent to which they are reimbursed. In addition to the issue of non-medical personnel reviewing records and photos, there is an issue of security where servers are broken into or files, taken home on laptops, are by third parties.

The point-of-care (POC) market generally refers to urgent care clinics, emergency room services, physician offices, and assisted care facilities, which are all staffed by trained health care professionals. These are federally regulated laboratories under the Food and Drug Administration (FDA) and Clinical Laboratory Improvement Amendments (CLIA); Federal law requires trained professionals to maintain and operate the equipment within compliance standards. CLIA regulated laboratories must maintain and disseminate data and test results within CLIA guidelines.

Over-the-counter tests are available for home care testing, e.g., drug screening, antigen testing, glucose testing, and urine testing. However, the number of tests is limited due to the special instrumentation and computer processing required. Glucose testing is one of the outlying cases where specialized instrumentation has developed to support testing at home; but, a system for selecting and running additional related diagnostic tests and comprehensive at home health care support system does not exist. More importantly, the physician typically makes the diagnosis, such as a diagnosis of diabetes, and directs the patient to self-test for glucose and also provides treatment guidance.

Health care costs continue to soar in spite of newer technologies purporting to reduce cost; primary care providers cannot support the 300 million people in the United States, and the spill-over is disrupting emergency care facilities. The medical paradigm of physician centric primary care is unable to sustain the quality of patient care administered two decades ago.

Digital Microscopy

Microscopy can be divided into three hardware categories: 1) Optical microscopy, wherein an enlarged sample image is displayed through an ocular assembly onto the observer's retina; 2) Digital microscopy, wherein a sample image is displayed onto a camera or other photosensitive device; and, 3) Hybrid microscopy, wherein an enlarged sample image can be displayed onto a retina or camera.

Digital microscopes are used to enlarge an object, for example a red blood cell in a whole blood smear, but are not designed for colorimetric or fluorometric laboratory assays such as glucose testing, antigen testing and the like. The design and operation of a digital microscope in a small form factor has extremely dense complexities; vibration from PC fans are transferred to the microscope slide, xyz translations and illumination must be conducted within the voltage and power constraints of the PC power supply, illumination and imaging paths must be substantially shorter, and image quality should be comparable to a standard optical microscope.

To reduce vibration, microscopes are set on a low vibration table. If an image is to be captured by a camera, the sample is translated into position and then time is allocated for the sample stage to settle down from the translation before the image is finally captured. A component of the translation vibration comes from stacking x and y translation tables upon one another. Each level, from the base to the top translation level, vibrates the level above it, and that vibration is magnified so that the top level vibrates the most.

Microscopes utilize an objective to collect, magnify, and infinity correct an image. The infinity correction serves to establish a light path in which other optical elements can be inserted with minor impact on the image. The tradeoff is a considerably larger objective size, more optical elements in the objective, greater difficulty in assembling and aligning the optical elements, and the need to extend the optical path beyond the objective, i.e., where an additional set of optical elements are required for image formation. Over the last 100 years microscope manufactures have moved toward lengthening the optical path, therein increasing the overall size of the microscope. An infinity corrected objective often requires a greater than 160 mm optical path.

In digital microscopy, many images are captured from scanning a microscope slide, which is assembled and displayed on an LCD display. The stage holding the slide is precisely positioned to enable image capture yet maintain image registration, i.e., of the tens of thousands of rows and columns all must be kept in perfect alignment. Current methods rely on the precision encoders and closed loop systems to determine movement distance, and they have based their methods upon the very high resolution of those encoders; they require better than 100 nm resolutions. They have developed slide coordinate systems that map encoder coordinates to locations on the slide, and they use those slide mapped coordinates for tiling and to avoid image overlap. The intent is that when an image is viewed on a display every displayed pixel has a corresponding coordinate on the scanned slide. However, when a slide is removed from a digital microscope and later placed back into the same position in the same digital microscope, the original encoder coordinates are no longer valid.

Relying on the fixed coordinate approach to scan and tile slides is costly, cumbersome, and fraught with error. Encoders are expensive and add complexity and points of failure. Moreover, others have confused encoder resolution with accuracy. It is not generally known that, although encoders have very high resolution (in many cases better that 20 nm), the absolute positional accuracy is only approximately 3,000 nm. Moreover, the absolute accuracy is only valid in a specific environment at a precise temperature. In a microscope stage environment, invariably the thermal gradients and transitions deform the metals holding the slide and encoder by 100,000 nm or more. Metal deformations degrade an absolute coordinate system.

Relying on encoders for abutting image tiles can lead to erroneous image results due to the absolute positional inaccuracy. For example, if a specific lot of encoders is used for deriving a coordinate system, and that lot is 3,000 nm longer than it should be, images collected and assembled based on that coordinate system will be distorted; this could possibly misdirect a clinical decision. This is especially true of line scan cameras.

With the transition to digital media and Internet transfer of medical records, there is a greater need for medical record security and tamper prevention. To detect tampering, digital images can be scanned for distortions using various algorithms known in the art. Certain acquisition distortions from encoder positional inaccuracies could be falsely construed as tampering.

Encoders that resolve better than 100 nm are primarily based on laser interferometry techniques. Encoders, in general, add cost to the system, increase the degree of electrical and software complexity increase assembly and maintenance costs, and add another possible failure point.

To assemble a macro composite of the entire tissue sample on a microscope slide, the tissue is first magnified thereby limiting the field of view to only a portion of the tissue sample. Those magnified images are tiled to form a larger magnified image of the entire tissue sample—a so called panoramic or composite image. At high magnifications, tens of thousands of tiles may need to be collected to form a composite macro image. Consequently, a physician that is only interested in the general appearance of one small section of tissue has to wait until the entire tissue is scanned and processed. Not only is this costly in time, but a typical pathology laboratory would generate terabytes of useless data that federal law mandates must be properly stored for many years, backed up, and security maintained.

Displays have a limited size and only a limited amount of information can be displayed. Superfluous images of virtual microscope slides, as is seen in the prior art, unnecessarily displaces important information. Displaying only the tissue sample, i.e., the object on the microscope slide, leaves room for other information.

There is significant programming and file overhead with the prior art coordinate based image tiling. A header file is needed for coordinate translation, and if lost or corrupted, image formation can fail. Additionally, image display is slow—when a file is downloaded from the hard drive it must first go through a coordinate translation algorithm that is unique to coordinate based image tiling to derive the image display coordinates.

Others have suggested methods for positioning by using overlapping images and correcting positioning errors by determining positioning error within the overlapping regions of consecutive images. Thus, two images must be captured that overlap. A mismatch in image registration is determined and translated into a coordinate offset error that is added to the position coordinates for the third captured image: wherein all three images are displayed. Consequently, rounding errors and offset error inaccuracies accumulate with every captured image. The accumulated error distorts both column and row alignment of tiled images. To overcome the distortion, each image must have a large number of overlapping pixels around the entire image periphery. Since each image includes positional error, capturing 50 images in one direction would require at least 50 times the positional error in overlapping pixels to compensate for accumulated distortion. This method requires a more expensive camera because of the extra pixels required to overlap images. Segmentation algorithms for calculating mal-alignment are inaccurate, slow, and computationally intensive. And, preprocessing images to strip out unused pixels in overlapping area around the image periphery requires significant computation time thereby further slowing down storage.

Image processing by the embedded microprocessor yields medically relevant information.

Electronic detection methods have advanced to the point where they are far more sensitive and less variable than the constituents in a biological assay. Biological assays have matured to a point where chemical species, proteins, and genetic components can be detected at the molecular level. However, such detection methods require a specific sequence of preparation that is beyond the training of the average person. In a hospital setting, where hundreds of samples have to be prepared each day, preparation and analysis is fully automated. Automation comes at a substantial price: capital equipment costs, federal regulatory certification costs, training costs, maintenance costs, and facilities costs. And, the automation equipment is not disposable. Consequently, many diagnostic tests cannot be run in small laboratories, physician offices, or at patient homes. This is especially true of PCR assays, where processing errors are poorly tolerated and the processing methods and temperatures are more complex.

Methods of moving fluids through pipes and channels have been around for centuries. In the last half of the last century, High Pressure Liquid Chromatography (HPLC) pioneered the miniaturization of fluid channels through the use of capillary tubing and rotary valves. Rotary valves generally consist of a set of disks of varying aspect ratios as layers and in contact with one another, which have channels in the intervening layers to divert fluid from an opening in the top layer to a predetermined opening in the bottom layer. Fluid will flow under pressure from the input through lateral channels to output. As the channels became smaller and smaller there was an exponential increase in force required to overcome surface tension, wall adherence, and maintain laminar flow. Air pressure, vacuum, column pressure, pumps, electromotive force, and centrifugation are required to move small volumes, especially for lateral movement—the fluid surface area for adherence to the wall exponentially increases as the volume decreases. Certain materials related to Delran and high molecular weight polypropylenes may reduce adherence but none eliminate adherence. Therefore, at small volumes, if a significant portion of the fluid surface is in contact with a channel wall (in proportion to the volume) pressure, something other than gravitational feed is required.

Many processes require a washing step to remove interfering constituents. Washing often uses centrifugation to pellet beads or cells or other constituents, and decanting the waste fluid. This is an extra procedural step that involves other equipment. A washing step limits the use of many assays to skilled personnel.

Many assays require thermal management—especially PCR assays where thermal management is complex. Thermal cyclers raise and lower temperature in discrete preprogrammed steps or establish annealing temperatures for primers. They can be heavy and costly, and they are not disposable. Reaction tubes containing the analyte must be in close contact with the thermal cycler for proper temperature control. The thermal contact issue is often problematic and can be overcome with PCR oil. This is one of the technical difficulties that has impeded the general introduction of genetic testing.

Size, durability, and reliability are focus issues for first responder emergencies e.g., anthrax release, bioterrorism, avian flu pandemic, where assays need to be run immediately without prior training, or in difficult terrain such as in a cave, or in a situation where diverting attention to the assay could prove deadly. Assays that are as small as a stack of coins can be stockpiled and moved in large quantities quickly. Small, fully automated assays which can be run by anyone without training both improve reliability and enables general availability of that assay.

Others of above ordinary skill in the art believe that "For medical applications requiring high resolution microscopy, such as pathogen detection, state of the art microscopic images are typically transferred to a computer and transmitted via the Internet for "telemicroscopy" or "remote microscopy" applications. The only device coupled directly to a cellular phone provides low numerical aperture optics and inadequate magnification and resolution for most microscopy applications."—United States Patent Application 2011/0009163, incorporated herein by reference in its entirety. While United States Patent Application 2011/0009163 teaches that high numerical aperture optics, high magnification and high resolution does not exist with cell phones, the present invention discloses a digital microscope that is small less than 2 liters in volume, weights less than 2 kilograms, has 3 axis motion control (x, y, z; movement and focus), has a numerical aperture (NA) of 0.85 (demonstrated NAs ranging from 0.10 to 1.45), has high magnification, has wavelength limited resolution, has brightfield illumination NAs matching demonstrated NAs, and can be coupled directly to a cellular phone for power and/or communications. Applications on the cellular phone directly connected to the invention support digital microscope control, communications to the network, and applications that convert images obtained from the digital microscope to clinical diagnostics. Moreover, the digital microscope system of this invention enables such features as bright-field, fluorescence, darkfield, oblique illumination, Hoffman contrast, differential interference contrast, structured illumination, polarization, confocal imaging and the like in the invention described above.

Others have alluded to high NA, high magnification and high resolution citing text book equations without out embodiment/enablement (e.g., United States Patent Application 2011/0009163). Without enabling information it is difficult to determine if it is even possible. Furthermore, without optical data information it appears that cell phones are set on top of a conventional microscope with conventional illumination and an image taken. Microscope objectives and the enablement of wavelength limited imaging or high numerical aperture or high magnification requires numerous basics for those of ordinary skill in the art such as Abbe number, lens radius, refractive index, etc. as are know in the art and exampled in hundreds of optical patents (e.g. U.S. Pat. No. 4,588,264; 0.7 NA microscope objective, incorporated herein by reference in its entirety). To enable the development of said optical assemblies with said numerical apertures or magnifications or resolutions, it is standard practice to place the variables in optimization software such as Zemax or Code-V to converge on the solution. Moreover, as the resolution begins to approach the wavelength limit, such things as group velocity dispersion, wave front, etc. become pivotal; and when unreferenced disallows enablement.

SUMMARY OF THE INVENTION

A digital microscope is disclosed that comprises a vectored method of collecting images from a digital microscope that is independent of the optical resolution and a slide based coordinate system, and a method of displaying those images and communicating those images over the Internet in a file format that does not require a header or prior knowledge of magnification, coordinate system, or tiling structure.

The present disclosure provides a very low cost system for at-home healthcare management, and an optional Internet linked professional and administrating supporting structure. Families unable to afford insurance will be able to run laboratory tests and address their own primary health care needs without the additional cost of monthly insurance premiums. It is contemplated that the home healthcare personal computer (HHPC) and tests could be purchased at a local drug store.

One object of the invention is to provide a system comprising a HHPC for diagnosing, testing, and managing the medical information derived therefrom, and adapted to connect to the Internet. Patients choose when and what tests will be run from the tests available in their home, what if any additional services may be required, what if any medical information will be shared, and as a result they derive their own diagnosis from tests, symptoms and personal experience. Within the HHPC is a digital microscope that provides colorimetric and microscopic imaging capabilities to support at-home diagnoses. Additionally, the HHPC provides an interface for gathering and processing data from physiological monitoring devices.

More specifically, a HHPC is disclosed that enables patients to diagnose and manage their health care, and manage their medical records. The object of the HHPC is to provide an interface for physiological testing, support Internet video and audio connections, and provide the capabilities for running laboratory tests. This is a departure from current health care management paradigms where diagnosis, testing, and medical record control resides predominately with physicians and their enterprise associations.

More specifically, and in relation to digital imaging, the present invention solves the problem of having to: 1) use large format cameras for the extra overlapping pixels; 2) use encoders for fine positioning; 3) contend with encoder induced image position distortion; 4) rely on a slide-based coordinate system; 5) employ computationally expensive algorithms for pixel alignment and pixel striping; 6) have prior knowledge of magnification and resolution for positioning, display, and internet transfer; and 7) having to discard images due to corrupted header files. The invention uses motion and velocity vectoring methods for capturing and tiling images using a digital microscope. Motion and velocity vectoring methods are fast and typically have better than half-pixel resolutions thereby fulfilling Nyquist requirements and mitigating error accumulation found in prior art pixel alignment methods.

With regards to processing samples for patients, the present invention provides a generic processing solution that utilizes a microscope slide for microscopic imaging and may have colorimetric indicators disposed to the slide that measures biological constituents. Specifically, the invention enables a vast array of methods and processes to be adapted to it, and can be conducted in an infinite combination of sequences. An additional embodiment includes processing automation utilizing a stacked arrangement that can transfer solids, liquids, or a combination, to different processing or analyses points. The invention accommodates thermal cycling, washing, mixing, optical analysis, filtration, partitioning, electrochemical analysis, and other processing techniques and analyses that are know in the art. In an illustrative embodiment, the invention receives a biological fluid sample for a multiplexed PCR assay. The invention preconditions the sample, adds probes to the sample and removes the preconditioning constituents, undergoes thermal cycling, and optically interrogates the sample to determine the concentration of specific constituents. And, the invention is miniature and disposable.

In an overarching illustration of the system, and illustrating the implementation of the optional insurance provider support, Health Care Management (HCM) insurers would provide patients with an at-home instrument for laboratory and physiological testing, an Internet link to professional and administrative support, and credit for five disposable tests per year per patient. When a patient feels ill, for an example a sore throat, the patient conducts the basic physiological tests, e.g., blood pressure and temperature, then runs a Strep Test (streptococcal) thereby using one of the five allocated tests per year. If symptoms are mild the patient may not wish to proceed any further, having assured themselves that they do not have strep throat. However, if symptoms or concerns are more severe the patient may run a Mono Spot test (mononucleosis). If the Strep Test was positive, the patient may opt to connect through the Internet to their insurer and have an antibiotic prescription sent to the nearest pharmacy (or have the pharmacy deliver the prescription to their home). The insurer provides other services over the internet as well; they may provide guidance and recommend additional tests, they may visually link the patient to a physician for a visual assessment or to answer questions, or they may recommend additional evaluation at a nearby medical facility, providing directions and making the appointment, or providing services to backup medical records and monitor progress. In my practice, most patients knew what was wrong and were seeking a confirmatory test and a prescription for relief. Moving primary care into the hands of the patients is more efficient and will greatly reduce insurance costs while improving health care. Today, patients are better educated, have access to vast amounts of medical information through the internet, and are capable of diagnosing most common illnesses, and have general knowledge of the therapeutics required having had or known others with similar illnesses.

One aspect of the invention is for primary care decisions to reside with the patient in their home. Those decisions include but are not limited to when to test themselves or a family member, what the starting diagnosis will be, what tests will be run, what additional tests will be run, whether connecting to the insurer for guidance is necessary, and whether and to what extent information will be shared with the insurer.

Another aspect of the invention is home testing, both physiological and biological parameters. Virtually all of the common physiological and biological tests are fully automated and commercially available to hospital laboratories and physicians. In one embodiment, separate equipment is utilized for testing as is known in the art. In an alternative embodiment, all testing is consolidated into a minimum number of testing instruments, preferably consolidated into one PC enclosure. Those tests include a group of physiological tests including, but not limited to blood pressure, multi-lead EKG, temperature, pulse oximetry, otoscope, ophthalmoscope, stethoscope, web camera, Doppler, fetal heart monitor, and others that can be designed to transmute a physiological metric to electrical data. Biological tests include but are not limited to colorimetric indicator assays both chemical and enzyme based, fluorescent assays, electrical impedance assays, image analysis assays, and others that are known in the art. Biological tests also include but are not limited to the following groups: assays of biological fluids, tissues, cellular/microbial/viral/parasitic constituents of blood, and genetic. Tests may be run individually, multiplexed, or as a panel of related tests. Panel testing is the preferred method because for example, related tests can be grouped onto one slide saving money and time for the patient.

Another aspect of the invention relates to the Internet link to the professional and administration support structure. A patient may choose to link to their insurance provider, at which time they can select specific services. They may elect to have their tests evaluated; the evaluation may lead to a prescription, recommendations for additional tests, or a directive to a health care professional for further guidance. Further guidance could include video linkage (and audio) for direct observation (for example in the case of: "Do I need stitches for this cut?"), or recommendations to visit a physician, urgent care center, or emergency room, along with maps, appointments, call for an ambulance, or other support. Administrative support can include billing services, technical support, data backup, health care monitoring, equipment updates, and purchasing of additional test panels.

DETAILED DESCRIPTION OF THE INVENTION

Figure 1:
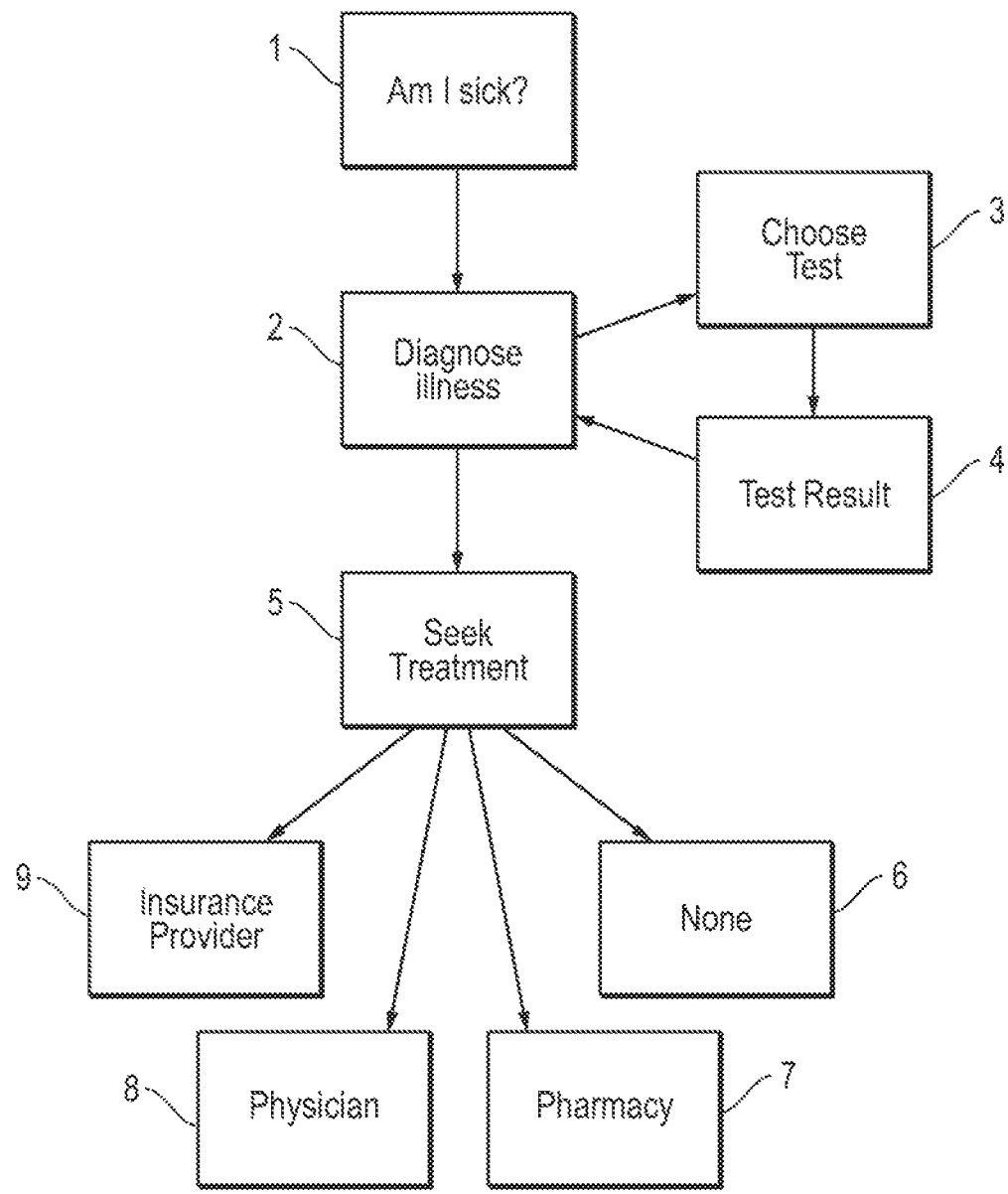
FIG. 1 illustrates a patient's decision process and the pathways to insurance provider support, according to an embodiment of the present invention.

The present disclosure provides a patient centric system wherein the patient is responsible for diagnosis, testing, management and medical records handling within their home, and wherein their insurer offers optional ancillary services through an Internet connection. Those services include, but are not limited to, test evaluations, consultations with professional health care providers, prescription services, medical records maintenance, and administrative services. A person of ordinary skill in the art will recognize that other services can also be provided with the disclosed system.

The system comprises a computer with interfaces for physiological testing, a digital Microscope for evaluating diagnostic tests, a connection to the Internet, and an optional insurer computer Internet connection that supports a network for data base and data storage, for connections to video and audio based consultations, and for administrative support.

The process of adapting a PC to receive a digital microscope by way of interfaces is known in the prior art. Such interfaces include, but are not limited to, USB, SATA and its variants, Ethernet, Firewire, IDE and its variants, SerDes and its variants, Bluetooth, WiFi and its variants, among others. According to one embodiment of the present disclosure, the digital microscope is connected via a USB port in connection with a device driver loaded from a CD. Also included on the CD is software for the user interface. The user interface provides support for communication over the Internet, drivers, the user interface to the physiological measuring devices, and software for home healthcare management.

The process of adapting a PC to receive data from physiological measuring devices is known in the prior art. Such interfaces include, but are not limited to Bluetooth, cell phone, USB, SATA and its variants, Ethernet, Firewire, IDE and its variants, SerDes and its variants, among others. According to one embodiment of the present disclosure, the physiological measuring devices are connected via a USB port in connection with a device driver loaded from a CD. Also included on the CD is software for the user interface. Other communications and downloads can be from the cell phone or personal communications device, the internet, or means known in the art.

The user interface collects the data from the physiological measuring devices, including the ID to identify the device, and displays the data on the PC display. For example, blood pressure data is received through the USB interface and the blood pressure is displayed on the PC display. Algorithms can be included that interpret physiological data. The user interface software controls the digital microscope much like a CD is controlled. For example, when a slide is inserted, the digital microscope retracts the slide, reads the slide label to identify the slide, then processes the slide based on the type of slide inserted—similar to the process for determining if an audio or data CD was inserted into a CD drive. Algorithms can be included that interpret the imaging and colorimetric results. Many of the interpretation algorithms are available as Freeware.

Referring now to FIG. 1 which depicts a patient decision tree, a patient decides if they are sick 1 and diagnoses their illness 2. Based upon the patient's diagnosis 2 they choose an appropriate diagnostic test(s) 3, which can be physiological, biological, or both. The test results 4 may direct them to a new diagnosis 2 and more testing 3, or the test results 4 may confirm the original diagnosis 2. At that time, the patient may seek treatment 5, which may include no specific treatment 6, or may require over-the-counter medicine from a pharmacy 7, visit with a physician 8, or an insurance provider support structure 9.

Figure 2:
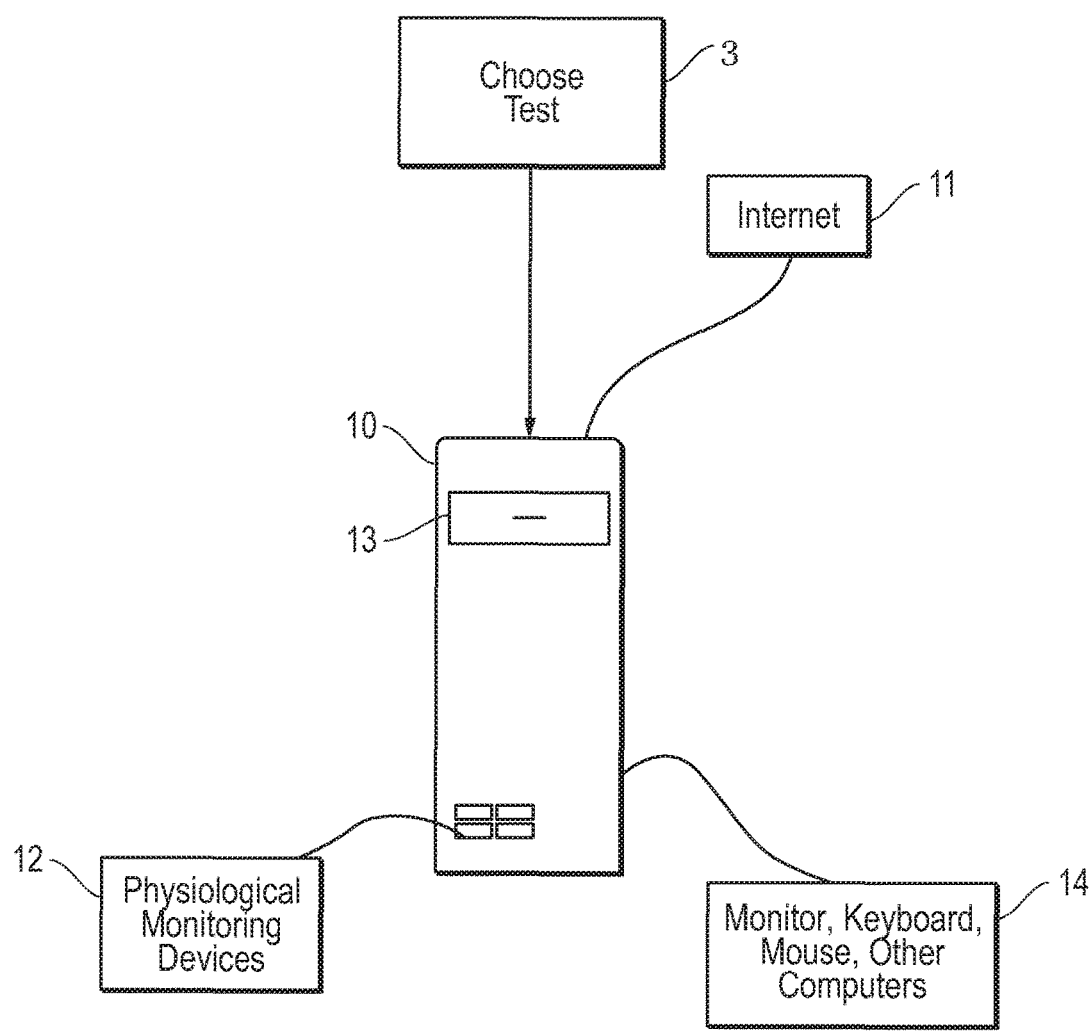
FIG. 2 is an illustration of a patient's computer with digital microscope, Internet access, and adapted to support data from physiological measuring devices, according to an embodiment of the present invention.

FIG. 2 is an illustration of a home healthcare management system depicting the patient and hardware interaction. In one embodiment, a CD size analysis device, such as microscopic imaging and colorimetric device 13, is inserted into a CD bay slot of a patient's computer PC 10. The PC 10 has USB ports and is adapted for interface communication attachment to a plurality of physiological monitoring devices 12 that include, but are not limited to, blood pressure devices, multi-lead EKG, temperature, pulse oximetry, otoscope, ophthalmoscope, stethoscope, web camera, Doppler, fetal heart monitor, and others that can be designed to transmute a physiological metric to electrical data. The PC 10 is also adapted to accept a microscopic imaging and colorimetric device 13, such as, but not limited to, a digital microscope. The PC 10 can be adapted to connect to the Internet 11 for providing other services including connection to an insurer's computer by means known in the art, and to other devices 14 such as, but not limited to, a keyboard, monitors, a mouse, and other computers.

Through the PC 10, the patient can select the appropriate tests 3 based on what they believe is causing their illness. Those beliefs can be substantiated from past experiences, through researching the possible causes of their symptoms, from probability-based algorithms, and/or through consultation with a health care professional. For example, they may choose to monitor temperature or take a blood test if they have a fever. If they are on blood thinners (e.g., coumadin) and have seen excess bruising, the patient may choose to check their coumadin level or clotting time. Additionally, the patient may wish to check something for informational purposes only, such as blood pressure during a stressful day or glucose levels when they feel hypoglycemic. Such tests will lead to an enhanced understanding of their own physiology, and thus early intervention.

The patient may also choose a test from a list of tests available in their home, and such list would include symptoms and diseases that the test is commonly associated with. The results of testing can be collected and displayed on an LCD monitor 14, along with additional tests that are available to the patient and are related to abnormal findings (symptoms and/or tests). For example, a patient may feel chronically tired and want to know if their thyroid is normal. As a result, they choose a general thyroid test. If the result of the thyroid test is abnormal, the PC 10 displays a set of tests that are related to the abnormal finding. There will always be a limited set of tests that can be conducted by the patient. A test centric algorithm would identify which tests are related to the patient's inquiry from the list of tests available on the PC 10. One such recommended test could be a blood test for anemia. Such relationships of tests to symptoms and abnormal test results to follow-up tests are well known in the art, and are further simplified by the limited number of tests that will be available to the patient. The instant invention of test centric test selection relates to the patient selecting tests from a limited number of tests available on their PC 10 and the iterative selection from said limited pool of tests, with or without guidance.

Figure 3:
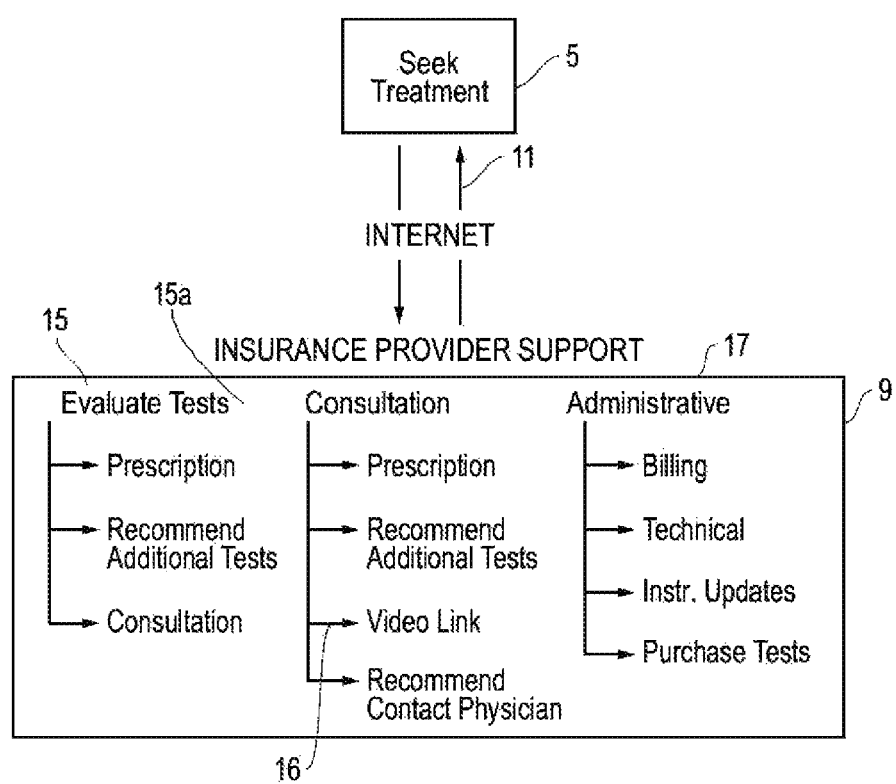
FIG. 3 is an illustration of the insurance provider support services, according to an embodiment of the present invention.

Now with reference to FIGS. 2 & 3, the patient's symptoms or the results of testing may indicate a treatment that may involve support from an insurance provider 9. A feature of this invention is an optional connection to additional services from an insurance provider 9 through the Internet 11. For example, during the course of testing the patient may have discovered that they have strep throat and thus require penicillin for treatment. The patient's computer PC 10 would display a menu option via 14 to have the test results evaluated 15. Results would be sent over the Internet 11 to the insurer's computer 9 where the results would be evaluated and a prescription generated and linked to a pharmacy 7 nearest to the patient's home, or the filled prescription can be delivered to the patient's home.

Alternatively, the patient may need consultation 15a from a health care professional, which may include but is not limited to a physician's assistant, nurse, occupational therapist, physical therapist, weight management professional, nutritionist, physician, oncologist, obstetrician, pediatrician, orthopedist, dermatologist, or other health care personnel. The patient would choose consultation from a menu display 14 and be linked to a health care professional through the Internet 11. For example, a patient may discover an unusual rough spot on their skin and be concerned that it is cancer. The patient would select a consultant from their menu display 14. A web camera via a video link 16 is connected to the PC 10 through a universal serial bus (USB) and is linked to an insurance provider's 9 computer though the Internet 11. The patient can interactively show the skin lesion to a dermatologist using the web cam via the video link 16, and the dermatologist can provide recommendations.

Alternatively, the patient may require administrative support 17 from their insurer. The patient would select administration from their menu display 14 and be linked through the Internet 11 to the insurance provider 9.

The insurance provider 9 possesses a computer comprising network devices and other devices for connecting to the Internet, databases, data storage devices, and other computers, as is known in the art. A multitude of services are provided to the patient through the network connection such as, but are not limited to, evaluation of patient tests 15, consultation services 15a, and administrative services 17. Subsumed within these services are various capabilities. For example, evaluating tests 15 may involve the generation of a prescription and additional links to a pharmacy. Or, test evaluation may be inconclusive requiring the patient to conduct additional tests or to consult with a health care provider. The decision trees to evaluate tests are created by the insurer based on the unique needs of the insurer and the tests offered. Methods and means of creating those algorithms are known in the art. Each service may have different trees and electronic connections that are known in the art.

In one embodiment for the patient's computer 10, the present disclosure provide for a single personal computer (PC) comprising, but not limited to, universal serial bus (USB) and Internet connections, and an imaging device for diagnostic slides. Physiological monitoring devices 12 such as temperature, EKG, otoscope, ophthalmic scope, pulse oximetry, blood pressure, and the like, are connected and powered by the USB. The USB is preferred because it provides power to the physiological monitoring device and thereby reduces cost and complexity of the device. The devices can then take advantage of the data storage, analysis capabilities, and Internet link resident in the PC.

As further detailed below, the imaging device for analyzing diagnostic slides comprises a light source, photodetection device, translation device to move the diagnostic slide and photodetection device into alignment, a diagnostic slide, and a connection to the PC 10. Lasers and LEDs are the preferred light sources. The photodetection device includes photodiodes individually or arranged in a CMOS or CCD array, avalanche photodiodes individually or arranged in an array, and electron cascade devices such as photomultiplier tubes and intensifiers. The translation device includes movement in the x, y, z and theta directions using, for example, stepper motors, servomotors, piezomotors, ceramic servo motors, and/or electromagnetic based translation. Alignment can be accomplished by moving the photodetection means or diagnostic slide or both, and correlating the alignment with increments of motor movement as is known in the art (e.g., steps in the case of stepper motors) and/or encoder feedback as is know in the art. Alternatively, the diagnostic slide may have positioning marks that are detected by the photodetection means and serve to adjust alignment. The photodetection device can further include imaging devices whereby the diagnostic slide is position based upon the image of the slide. The diagnostic slide can be supplied to the patient by the insurer or in partnership with a retail distributor (e.g., a pharmacy chain). In one embodiment, the slide is a microscope slide with diagnostic tests disposed to the slide, upon which the patient applies a body fluid (e.g., blood). The slide is moved into the PC and positioned within the optical path of the photodetection device by the translation device, and colorimetric and/or imaging data is collected by the photodetection device. Colorimetric data refers to different wavelengths of light including fluorescence, and imaging data refers to different wavelengths of light including fluorescence collected as a two-dimensional array. Colorimetric methods for determining the presence of constituents in an analyte are known in the art and many are commercially available. Examples include, but are not limited to, ELISA based assays, fluorometric assays, enzyme assays, chemical assays, chemoluminescent assays, PCR assays, hybridization assays, genomic assays, protein assays, and the like. By illustration, a pregnancy test strip disposed to a diagnostic slide, and a volume of urine placed on the test strip, would turn color if the urine was from a pregnant patient. The slide is inserted into the patient's PC analysis device 13 and translated to the photodetectors whereby the color change would be detected. For imaging, a drop of blood is deposited on the slide and translated to a photodetection array, and an image of the blood is collected by the patient's PC analysis device 13. Image evaluation algorithms are known in the art and commercially available that will count the cells in the image and classify them e.g., red blood cells, white blood cells, basophiles, granulocytes, neutrophils, sickle cells, abnormal cells, parasites, and other solid blood constituents.

In another embodiment, diagnostic tests are grouped onto the same slide. For example, a prostate specific antigen (PSA) test strip is disposed on a slide and a drop of blood placed on the slide such that the drop covers part of the strip and part of the slide. After proper positioning, the photodetectors determine if the PSA test strip has turned color (colorimetric test), and the drop of blood is imaged, classifying the cells found in the blood. Test strips can be reduced in size so that many strips can be disposed to a single slide while at the same time an image can be collected of constituents in the applied body fluid e.g., multiple urine test strips disposed to a slide for colorimetric data, and an image collected to analyze for bacteria, blood, or cancer cells in the urine. The present invention can be the combination of image analysis and colorimetric analysis of the same body fluid volume in a single PC, and without the need for other instruments. Furthermore, tests can be grouped into a panel of tests that compliment one another. For example, all possible urine tests would be grouped onto one slide for convenience, or different tests grouped together for sore throat or flu like symptoms, or for a specific age group e.g., geriatric tests for heart medicines, blood thinners, cholesterol, and the like. Although the present invention may be applicable to a variety of imaging and analyses methods, it is particularly suited to home healthcare management.

Figure 4:
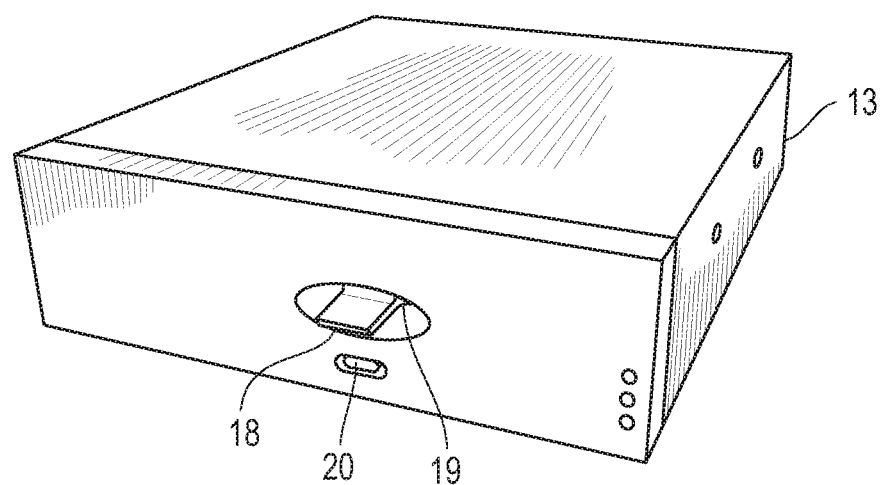
FIG. 4 is an illustration of a PC analysis microscope device adapted for use in the compact disc bay of a PC, according to an embodiment of the present invention.

An illustration of a PC analysis device 13 that uses slides for analyzing biological constituents and fits into a personal computer can be seen in FIG. 4. Once placed into the CD bay of a PC 10, the PC 10 and the PC analysis device 13 become the HHPC system. For at-home testing, a slide 18, with for example a drop of blood on the surface, is inserted into the PC analysis device 13 through an opening 19 for analysis, and retrieved using an eject button 20. The PC analysis device 13 acquires colorimetric and image information from the slide 18 using photodetection means and analysis means known in the art.

Figure 5:
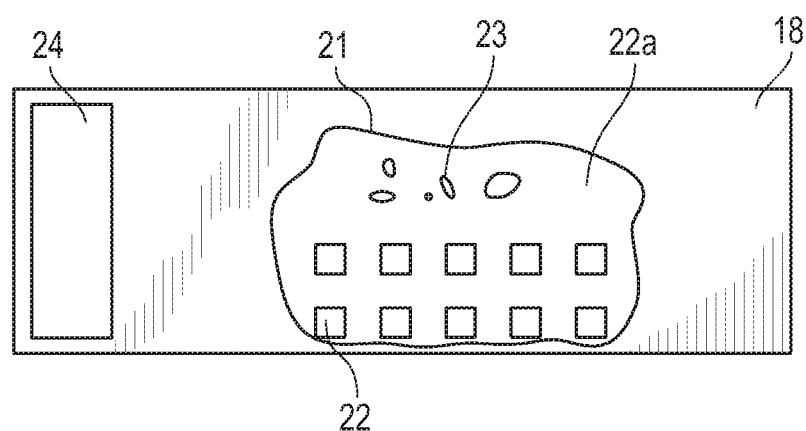
FIG. 5 is an illustration of a slide having colorimetric indicators for analysis and an area for imaging constituents, according to an embodiment of the present invention.

The slide 18, in FIG. 5, illustrates how a panel of colorimetric tests 22 can be organized on a slide 18. By way of illustration, a biological fluid, for example urine 21, can be placed on the slide 18 to cover the panel of colorimetric tests 22 and an open area 22a of the slide 18 for imaging. The imaging area can be used to detect constituents 23 in the urine such as blood, bacteria, cancer cells, crystals, cell ghosts, and the like. The slide 18 may have a barcode 24 affixed to it that conveys information about the test and patient, such as calibration points, location of tests, type of tests, patient record number, lot number, etc. The slide 18 is one envisioned embodiment for a receptacle that collects and analyzes fluid, cells and tissue. Other receptacles are contemplated and within the scope of the invention. Such receptacles could provide processing means for preparing the analyte for analysis, using the same computational means and taking advantage of the translation means.

Figure 6:
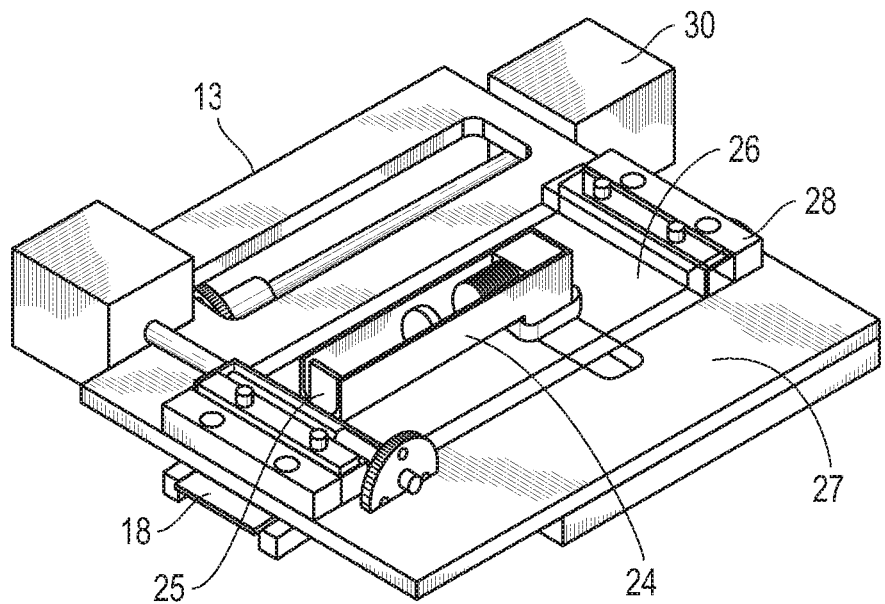
FIG. 6 is a top view drawing of the mechanical and optical components of the PC analysis microscope device, according to an embodiment of the present invention.
Figure 7:
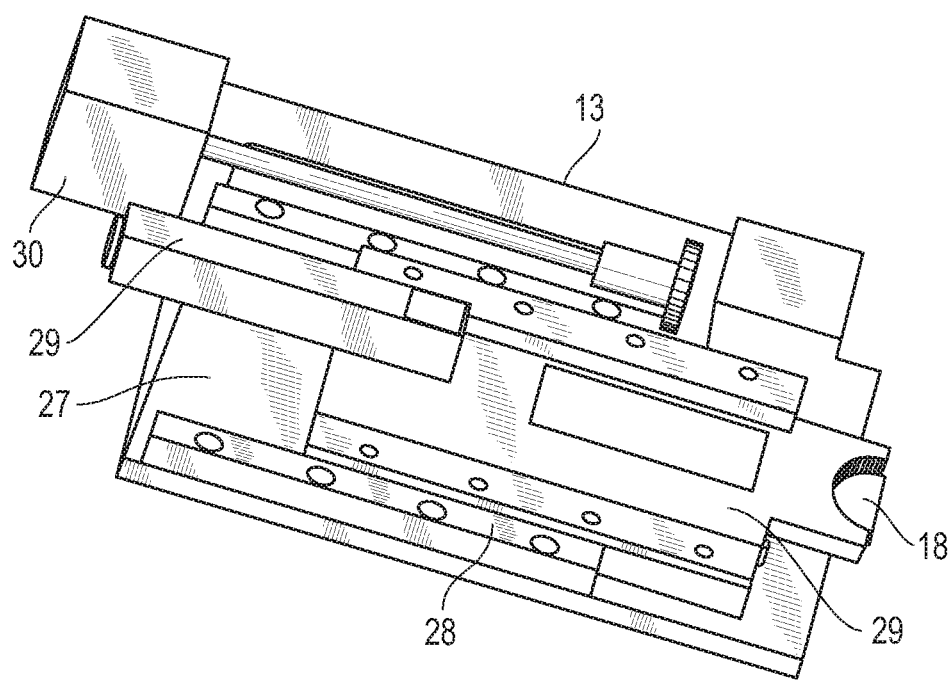
FIG. 7 is a bottom view drawing of the mechanical and optical components of the PC analysis microscope device, according to an embodiment of the present invention.

FIGS. 6 and 7 are top and bottom views, respectively, of the illustrative PC analysis device 13. A feature of the instant invention is a shortened optical path 24 leading to a photodetection device 25. Photodetection for a magnified image requires a shortened (less than 160 mm) optical path to fit into a CD bay form factor. That path may be shortened through folding the light path with one or more mirrors, the use of a shortened objective, or both. It can also be shortened by adjusting the output image to fit the photodetection means. Adjusting the image to fit the photodetection means serves to reduce the magnification requirements, decreases the cost by reducing the number of optical elements required for imaging and infinity correction, can improve image contrast by using <100% fill factor, and can improve the sensitivity and specificity of algorithms that rely on contrast for image analysis.

Figure 8:
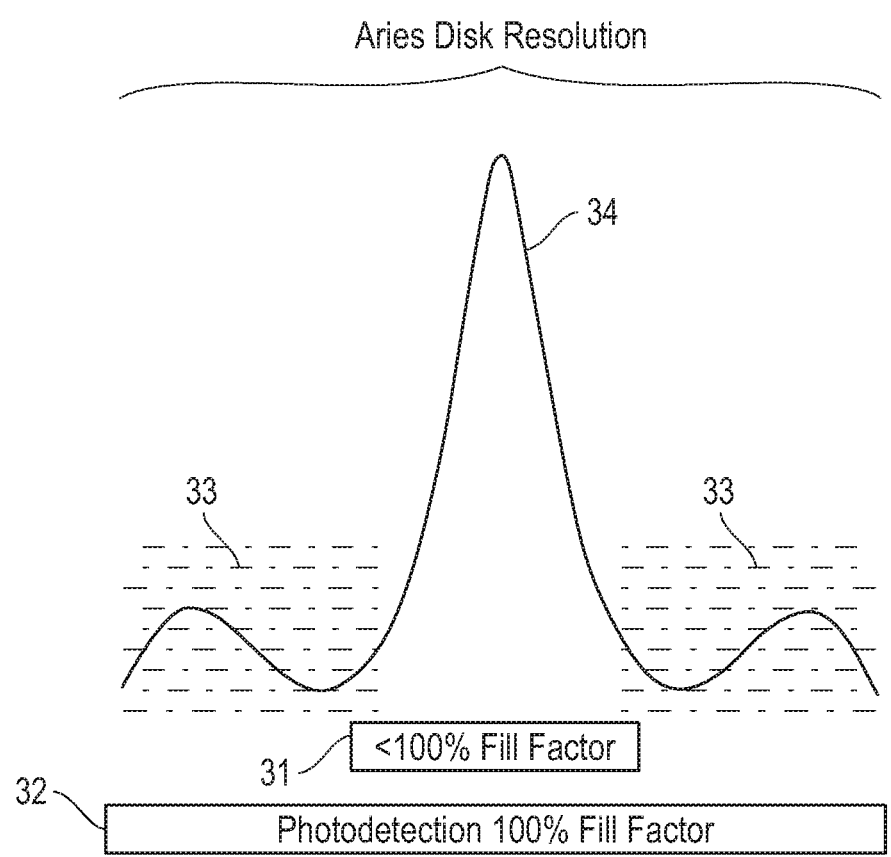
FIG. 8 illustrates Aries Disk resolution and the area collected to increase contrast and reduce magnification using a <100% fill factor photodetector, according to an embodiment of the present invention.

To adjust the image to fit the photodetection device 25, the diffraction limit of optical assembly is determined by computer design modeling, for example using CodeV as is known in the art, or by using commercially available calibration targets as is known in the art. For example, if the system were found to have a diffraction limit of 300 nm at a wavelength of 500 nm, a 300 nm object would be imaged onto a <100% fill factor pixel in a photodetection means. Since the fill factor is <100%, some of the light from the 300 nm object imaged onto the pixel area would be discarded. In this example, the 300 nm object represents the Aries Disk resolution FIG. 8. To enhance contrast, the present disclosure provide a device that scales the photodetection area 31, a subset of the pixel area, to collect only a portion of the Aries Disk distribution, i.e., the high frequency portion. Prior methods strive for 100% fill factor 32. In an effort to enhance contrast, a portion of the image is discarded 33. One can match the fill factor requirement by substituting different fill factor detectors until the contrast is optimized. Alternatively, the fill factor requirement can be quantitatively determined using Sparrow or Dawes criteria for defining the extent of the Aries Disk 34 required for optimized contrast. The Nyquist aliasing induced by discarding light can benefit image analysis techniques.

The present disclosure provides for reduction of magnification requirements while maintaining comparable resolution. In matching the image collection optics and resolution to the detector, several advantages are realized: the optical path length can be shortened to less than 160 mm; the cost of the optical assembly is reduced; and, the magnification requirements are reduced. For example, most microscopes use 60×, 80×, or 100× objectives for wavelength limited resolution i.e., 300 nm resolution at a 500 nm wavelength. In the present device, a 300 nm object imaged onto a commercially available photodetector having 1750×1750 nm pixels would require a magnification of ~5.83~(e.g., 5.83×300 nm≈1750 nm). Thus, the present disclosure provides for substantially less than 60× magnification for wavelength limited resolution in a digital microscope.

The photodetection device is translated along the short axis of the slide 18 (herein referred as x translation). The x translation means 26 is attached to a base 27 through conventional cross-roller bearing rails 28, and has the light supply (29, FIG. 7) attached to the translation stage 26. Thus, the optical axis can be translated independent of the slide 18 movement. The present disclosure provides advantages over previous methods by having the x stage 26 and y stage 29 share a common base 27 thus imparting a unique vibration reduction method. Vibrations from the PC 10 cooling fans are transmitted through the base 27 (which attaches to the PC) and are distributed to both the x stage 26 and y stage 29 to cancel each other in the collected image.

FIG. 7 is a bottom view illustration where the drive device 30, in this example a stepper motor, and the LED illumination device 29 can be seen. The present disclosure provides for an LED in a folded optical path that fits in a CD form factor, having an optical path of less than 130 mm.

The current practice to achieve the required translation precision is to use linear actuator screws, piezoelectric means, and/or motor and precision screw combinations. This is typically done in a closed loop configuration using encoders, as is known in the art. Prior methods teach against the use of gears due to the inherent lack of translational precision. The highest gear tolerance standards are far inferior to piezoelectric and precision screw means, by both backlash and error. However, disclosed herein is a unique combination of a geared translation device, calibration and image collection that enables digital microscopy at a very low cost, and very small enclosures. 120 diametric pitch (DP) gears are utilized for both x and y translation. The gears are disposed to a stepper motor configured for microstepping. The microstepping feature of the stepper motor in combination with the 120 DP gear achieves sub-micron resolutions. Springs, gravity, force vectors, elastic means, anti-backlash gearing, or other means known in the art can add preload to mitigate backlash. An embedded processor means is used to control translation and move the slide stage to a known starting point (calibration) in both x and y axes. The same x and y translation process control is used to add backlash compensation to further enhance translation precision, which can range from no compensation to significant compensation. A special image capture strategy is required for image capture and stitching. Imaging of adjacent areas requires that the images overlap in their field of view. The overlapping of edges is used to insure that there are no empty gaps between consecutive images caused by gear translation imprecision (e.g., gear error or backlash). The instant invention is a very low cost small digital microscope which utilizes a combination of gearing for x and y translation, software backlash compensation, and an overlapping image collection strategy.

In one illustrative embodiment, a patient has the symptom of burning during urination and concludes that they have a urinary tract infection, because they have had several in their lifetime with the same symptoms. That patient obtains a slide with a panel of colorimetric tests that are associated with urinary tract infections and an open area for imaging. The patient places urine on the slide, and places the slide in the CD-M Scope. During analysis of the slide using means that are known in the art, the patient checks their temperature using a physiological monitor that plugs into the USB port. If the analyses are all negative and their temperature is normal, they may assume a minor irritation and choose to wait another day to see if the symptoms subside before conducting additional at-home testing.

Figure 9:
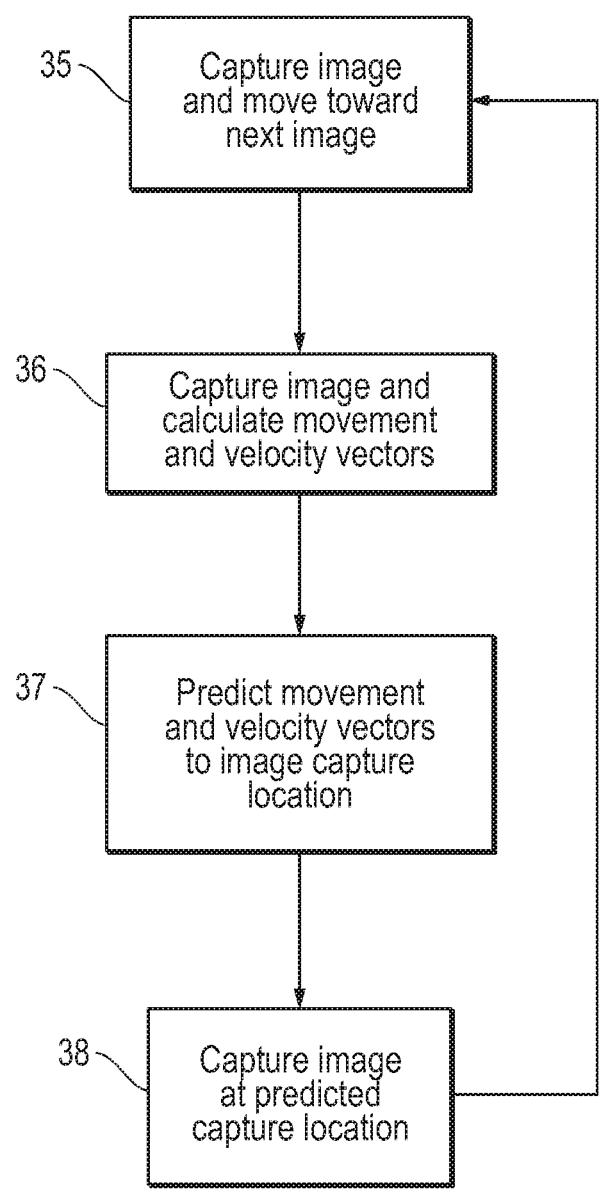
FIG. 9 is a flow chart diagram of a vectoring process, according to an embodiment of the present invention.
Figure 10:
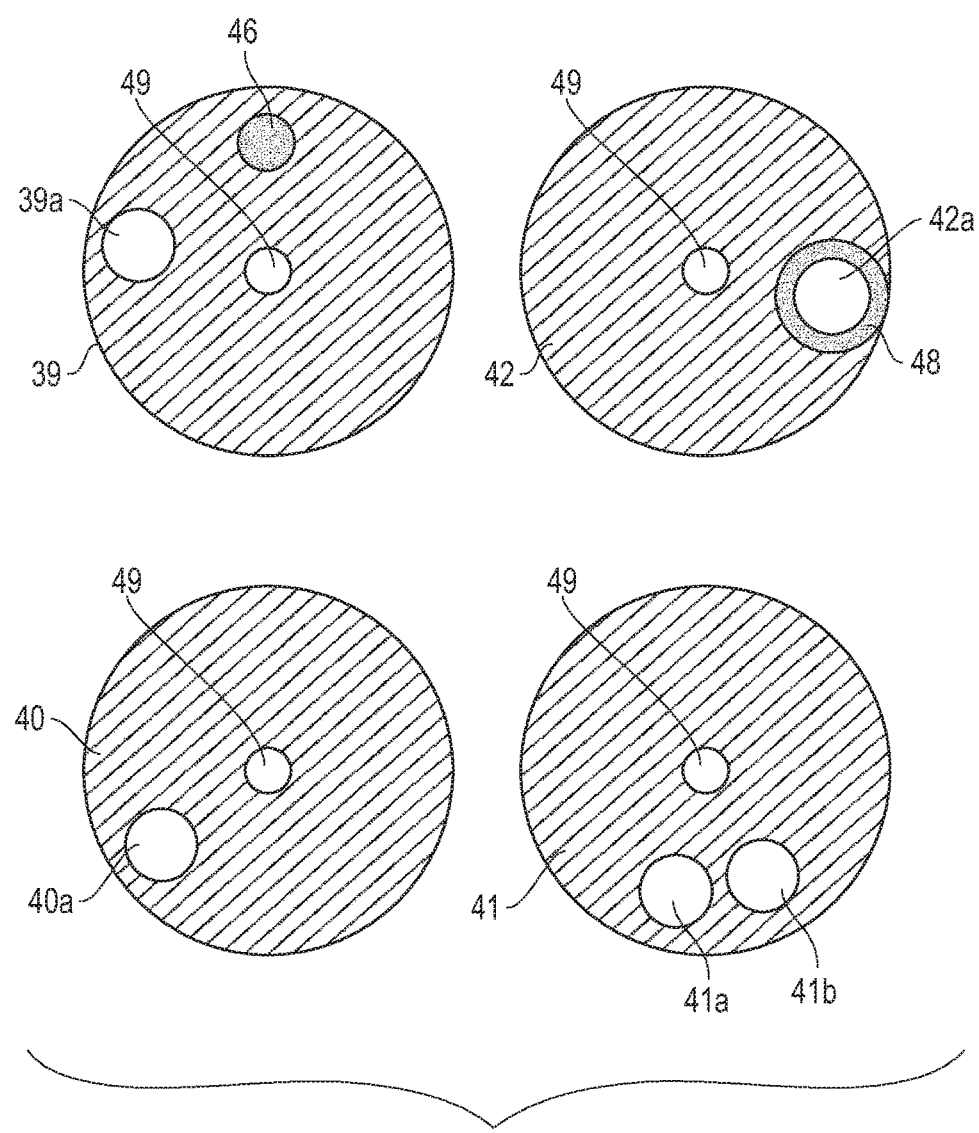
FIG. 10 is top view illustration of four disks that can be stacked to form an automated processing system, according to an embodiment of the present invention.
Figure 11A:
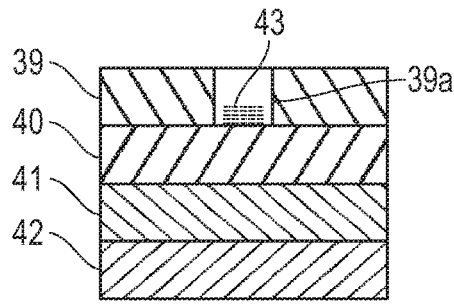
FIGS. 11a-11f are side view illustrations of one embodiment wherein disks are stacked showing a sequence of alignment and processing steps, according to an embodiment of the present invention.
Figure 11D:
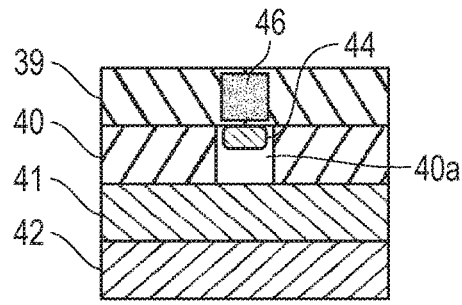
Figure 11B:
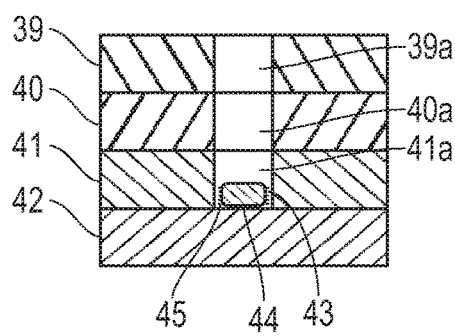
Figure 11E:
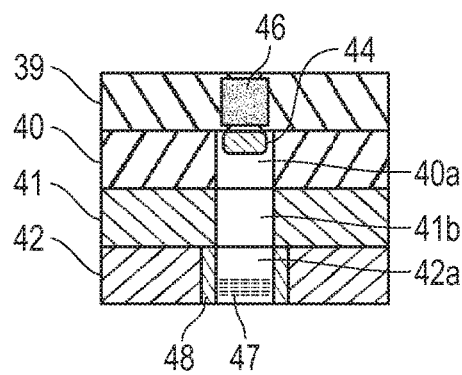
Figure 11C:
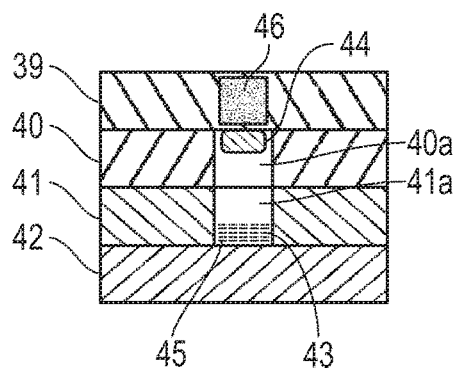
Figure 11F:
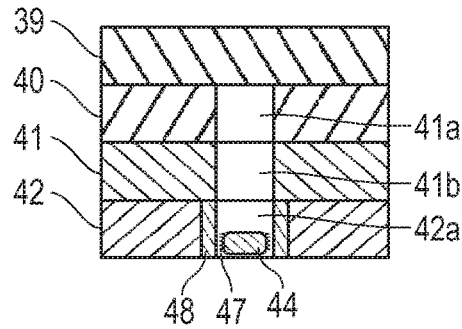

FIG. 9 shows a flow chart diagram of the vectoring process used in one embodiment of the present invention. A digital image is captured of, for example, tissue on a microscope slide, and imaging is then moved toward the next adjacent image capture location 35. During movement, a second image is captured to calculate the movement and velocity vectors 36. Methods and hardware for calculating movement and velocity vectors are known in the art. A common example of determining movement vector and velocity resides in a typical optical trackball mouse where high contrast points of the rotating ball are captured and the movement vector and velocity are used to position the pointer on a display. (Methods to calculate movement and velocity vectors, and predict for example "when the train will arrive at the station", are widely available in high school and college text books.) Once the movement and velocity vectors are determined, the time required and vector required to move to the next desired image capture location can be predicted 37. At this time, the movement vector may be optimized to arrive at the desired location, and the time to arrival may be recalculated. Upon passage of the predicted amount of time and arrival at the predicted location, a subsequent image is captured 38 and the sequence is repeated.

In an illustrative embodiment, a 640×480 pixel camera (VGA camera) is used to collect images. An image of tissue on a microscope slide is captured and the image is moved to the right by a motor means—in this illustrative embodiment there is no coordinate system so left and right are arbitrary references. During movement, a second image is captured and processed to determine motion and velocity vectors. The calculations indicate that the movement is in the desired direction at a velocity of 1,000 pixels/second and will arrive at the desired location in 0.5 seconds. 0.5 seconds later a subsequent image is captured and the sequence is repeated.

In one embodiment, images are captured without overlap because each image is captured at the desired location. Thus, raster scanning of a large area would yield images that could be tiled to view the entire image without further processing to align pixels or strip overlapping pixels. It is herein contemplated that the image collection direction can be randomly driven by an operators desires.

In an alternate embodiment, video streaming is used to collect images. For example, tissue is raster scanned with a digital microscope and the digital images streamed to a processor (for example, a personal computer) by means know in the art. The motion and velocity vectors are calculated from the streaming frames. Based on the motion and velocity vectors positioning can be adjusted, and the frame to capture next can be predicted. In an alternate embodiment, the video stream can be sampled to determine motion and velocity vectors, and a subset of pixels that are predicted to have maintained the proper horizontal and vertical alignment can be saved. While this embodiment would require a larger format camera, only the aligned pixels from predictions would be saved for tiling, i.e., motion and velocity vectors would be used to predict which pixels in the video stream would be aligned at the predicted capture location.

In one embodiment for collecting images and tiling those images to form a larger image, a digital microscope can be used. A digital microscope is an instrument that magnifies an image and captures that magnified image with a digital camera. In one embodiment, the optics and camera are compacted into a personal computer compact disk bay form factor enabled by the synergies of moving both the optical collection assemblies and the slide. An example of this can be seen in provisional application No. 60/865,872, incorporated by reference herein. A slide with tissue is placed into the digital microscope and at least 2 images of the tissue are captured—a first image and a second image as the digital microscope moves toward a different location. A motion and velocity vector is calculated using the two captured images. The calculated motion and velocity vector is used to predict the motion vector and time needed to get to the next image capture location. For example, if the camera is a 1024×1024 pixel camera, and the image is moving horizontally during a raster scan, then the next image capture location will need to be a total of 1024 pixels away in the same horizontal direction. When the predicted time is reached, and imaging is at the predicted capture location, a subsequent image is captured (for a total of 3 images in this example). The first image and the third image of this example are saved and can be horizontally tiled thereby providing a larger image. Raster scanning using this method will yield a row and column matrix that can be tiled to form a larger image based on the image's row and column capture location independent of the slide coordinate system or magnification.

In an embodiment for transferring the images over the Internet and communicating how the tiles are assembled to form a larger image or composite image the file name of the image has two major parts, the name and the extension indicating the type of file. In the present disclosure, the name would consist of 3 features, a name unique to the group of tiles that will be assembled into a larger image, and the position in the column and row that the image would take once assembled. For example, "MAGEr120c10.jpg" would belong to the IMAGE group and have a jpeg file type. The tiling location would be at row 120 and column 10. Fractions of rows or columns could be used as the hand to indicate a partial frame shift in tiling. File names with column and row designations can be assembled without any information on image size, image magnification, or image coordinate system. Moreover, assembly does not require an additional header file. All files are independent and if any one or more are lost or corrupted the larger image can still be assembled. Only the corrupted tiles may be lost, which is advantageous in the field of Internet communications where packets are often dropped. Provided by the present disclosure are faster disk access and general use, because the file name includes the column and row location (and, does not require special algorithms to map tile location to a slide coordinate system). Therefore, in contrast to prior art, the file name can be bit masked to provide the tile column and row location in the display—the fastest operation that a computer processor is capable of doing. In a further improvement in speed, the file name can be bit masked to become the pointer to personal computer memory space locating all the images in a large image assembly, which is a process many fold faster than the current art.

In an alternate embodiment, images can be formatted for use in the Keyhole Markup Language.

Traditionally, in cell and tissue imaging, the observed nuclei are dense having an optical density sometimes greater the 5 optical densities (OD). The optical density is also dependant on the thickness of the sample. Microscopes are aligned and light intensities set to highlight the features of the low density tissue constituents, essentially reducing nuclei features to a black dot. Highlighting subtle cellular features and reducing nuclei images to dense black dots further enhances the abilities of algorithms to detect and count nuclei with contrast detection algorithms, therein improving the ability to automate diagnosis. In the instant invention, nuclear detection algorithm performance is degraded through the use of high dynamic range imaging. High dynamic imaging of, for example, cellular tissue and other microscopic material is defined as having a dynamic range greater than or equal to 100 dB. The present disclosure provides for the use of high dynamic range imaging of microscopic material. In digital microscopy, contrast is defined as the rate of change in intensity over a pixel distance. A high dynamic range image detector array, having a dynamic range greater than 100 dB, can be placed in the imaging path of a digital microscope. The illumination intensity and alignment can be adjusted by means known in the art to visualize both the less dense material, e.g., intracellular material, and the high density material, e.g., nuclei. While nuclear contrast is decreased, intra-nuclear detail is revealed. Intra-nuclear detail does not have definitive diagnostic implications in tissue in the current art, but someday could be utilized adjunctively in a diagnostic decision tree. Current applications in hematology, and dense staining methods such as HER2/neu immunostaining, do not utilize high dynamic range digital microscopy. However, as computer processing power increases, algorithms for detecting features in low contrast samples will be developed. The instant invention is a method whereby a high dynamic range CMOS detector is placed in the imaging path of a digital microscope have electronic means to move in at least 3 axes, x, y, and z, and a digital image captured from said CMOS detector. The captured image could be transmitted over a network, stitched with other images captured from said CMOS detector to form a larger image, and/or directly displayed on a monitor. Stitching means have been in the art since the 1950s.

In a novel embodiment, which has not been done in the history of microscopy, a continuous focus camera with predictive focus was used for real time image collection on a digital microscope. In prior art, image collection followed the discontinuous and deterministic steps of: 1) triggering image acquisition; 2) image packaging for transmission; 3) transmissions; 4) unpacking transmitted image; 5) image processing for autofocusing; 6) packaging the autofocus for transmission; and 7) triggering the acquisition of the next image. In the current invention image acquisition and autofocusing is continuous without having to go through triggering communications, packing protocols for transmission, nor using various buss protocols. Instead, for example, an OmniVision camera with built in autofocusing is placed in the digital microscope's imaging path and programmed to continuously adjust focus. In this embodiment, the autofocusing signal is monitored for steady state, thereby indicating that the image is focused. Once autofocus steady state is reached, determined by the lack of substantial change in the autofocus position, the current image output is collected discarding the other images. The instant invention has the advantage of being substantially faster, easier to implement, reducing the time lag implicit in transmission protocols, and being an independent process unaffected by other ongoing processes that could delay conversion to an autofocused conclusion. Specifically, an imaging array with built in autofocusing capabilities, e.g., OmniVision and the like, is disposed to a digital microscope in the imaging path for acquiring images. The autofocusing imaging array is disposed to a motion translation means that controls the location of the sample relative to the imaging objective along the digital microscope's imaging axis. Images are continuously acquired by the imaging means, and a figure of merit for image positioning is determined utilizing the image data. Methods to determine figure of merit from image data are known in the art, and in this invention are programmed into the sensor chip. Also known in the art is a means to adjust the sample location in the imaging axis based on the figure of merit so as to obtain the clearest focus. Based on diminished motion of the sample translation in the imaging axis, or no motion at all, the continuous stream of image data is sampled so as to acquire the focused image. In other words, the camera is continuously sending image data out of the camera, and as it captures images it continuously updates the autofocus figure of merit based on the current captured image. Of all the images that are captured only a few will have a suitable figure of merit or a substantially unchanged figure of merit from one captured image to the next. Therefore, the instant invention is a method to sample the image capture output of a camera having an autofocus figure of merit, and wherein said camera controls the autofocus translation means. The invention increases the speed of collecting in-focus images and reduces the bandwidth requirements for collecting the images because only the captured in-focus images (best figure of merit) are collected. Thus stitched images can be obtained to form a larger image (stitching methods are known in the art). In an alternate embodiment, the imaging array is connected to a companion processor by means of a parallel port data connection, and image data is directly transferred to the companion processor for continuous autofocusing. The companion process has the unique features of having a direct parallel connection to the imaging array and an internal feature that determines an autofocus figure of merit. A direct parallel connection between the companion processor and the image array mitigates the need for handshaking protocols used to transfer data on common buses. Other than physical separation, the companion processor/image array functions in the continuous autofocus method as previously described.

In an embodiment for an x and y translation motion invention, a microscope slide stage is disposed to piezoelectric motors having members for motion translation in the same plane as the microscope slide. Typically, piezoelectric motors are perpendicular to the microscope slide plane, providing motion with the gravitation vector serving as a small preload perpendicular to the motion control plane (frictional translation forces are perpendicular). Moreover, the piezoelectric translation elements are not disposed to the microscope slide stage, but fixed to a separate fixture. Alternatively, in the instant invention, the frictional vectors and gravitational pre-load are in the same plane. Thus, rather than using frictional forces of the piezoelectric movement to overcome gravitational forces, gravitational forces are utilized synergistically to hold piezo-elements in juxtaposition to frictional elements. The dual synergies of using gravity and the sandwiching design needed to support a parallel plane approach results in cost savings, power savings, size savings, and quicker more agile motion. The simplicity of the sandwich parallel plane design reduces assembly costs and increases reliability.

The digital microscope of the present disclosure can be adapted to accept a processing platform, for image and colorimetric analysis, wherein different procedures, processes, and analyses are conducted. One embodiment includes a disk shaped stack—because the size is reduced; however other embodiments such as a bar are contemplated. The top and bottom are referenced to the gravity vector. FIGS. 10-13 are related illustrations. In the FIG. 10 (top view), the top disk 39 is followed by disks 40, 41, and 42, 42 being the bottom disk. Each disk revolves around its annular axis 49. Disk 39 has a cavity 39a that can hold fluid or a solid, and a magnet 46. Disk 40 has one cavity 40a. Disk 41 has two cavities 41a and 41b. The bottom disk 42 has one cavity 42a within a thermally conductive liner 48 for thermal cycling.

In FIG. 11 (side view), the disks are stacked and a processing example is illustrated. A sample, for example blood, can be placed in cavity 39a, FIG. 11a. That cavity 39a may contain a reagent 43 that prepares the sample for analysis. The sample is then incubated in the reagent. After incubation, disks 39, 40; and 41 are rotated FIG. 11b, aligning cavities 39a, 40a, and 41a. In cavity 41a are ferrous beads 44 with molecular probes attached, and a second reagent 45. Reagent 45 and sample are gravity feed to combine with reagent 45 and beads 44. After a suitable incubation, disk 39 is rotated to position a magnet over cavities 40a and 41a (FIG. 11c). The magnetic attraction 46 lifts the beads 44 out of reagents 43 and 45. Disks 39 and 40 (FIG. 11d) are rotated, moving the beads 44 and what has bound to the beads from the sample. Then disks 41 and 42 (FIG. 11e) are positioned to align cavity 42a with cavity 41b, cavity 40a, and the magnet 46, thereby positioning the beads 44 over a new reagent 47. Disk 39 is rotated (FIG. 11f) thereby removing the magnetic 46 forces from attracting the beads 44, and the beads are deposited into reagent 47. Surrounding cavity 42a is a thermally conductive material 48, such as copper, used to adjust the cavity temperature. In genetics analyses it can serve as a thermal cycler.

Figure 12:
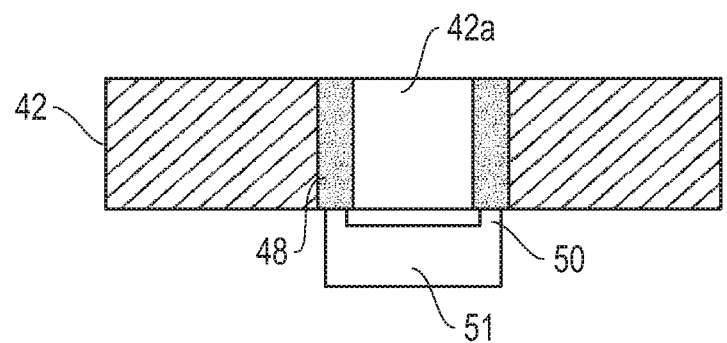
FIG. 12 is a side view illustration of a disk with a thermal cycler, according to an embodiment of the present invention.
Figure 13:
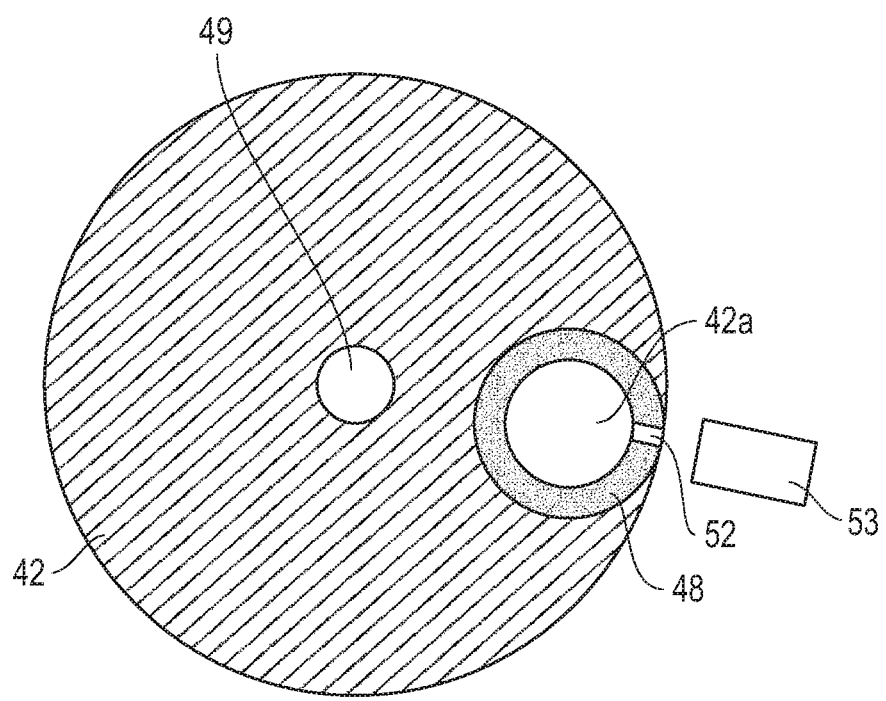
FIG. 13 is an top view illustration of a disk with a window for optical analysis, according to an embodiment of the present invention.

FIG. 12 is an example of disk 42 having rotated to position the thermally conductive element 48 to be in contact with a thermal conduction means 50 attached to a thermal electric cooler 51. Reactions can be monitored during thermal cycle, as shown in FIG. 13. The thermal conductor 48 surrounding cavity 42a can have a window 52 to optically monitor 53 the process.

Figure 14A:
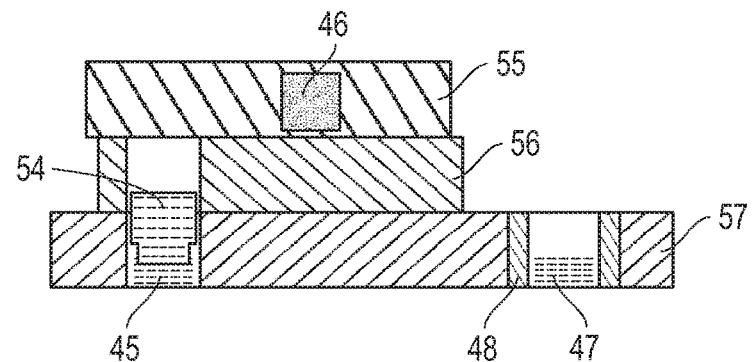
FIG. 14A-C are side view illustrations of an alternative embodiment whereby linearly translating bars replace disks, according to an embodiment of the present invention.
Figure 14B:
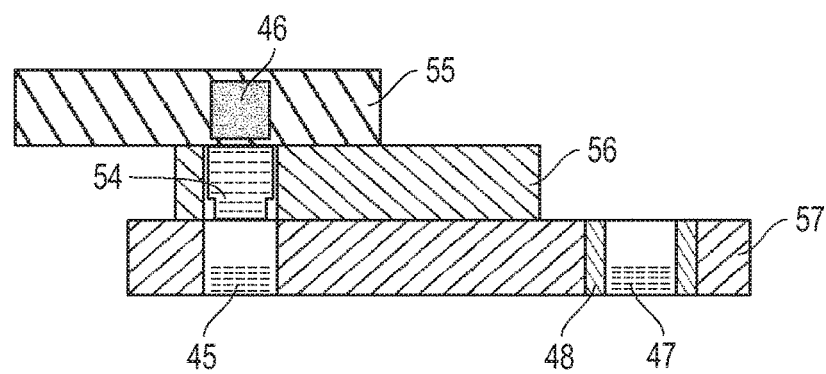
Figure 14C:
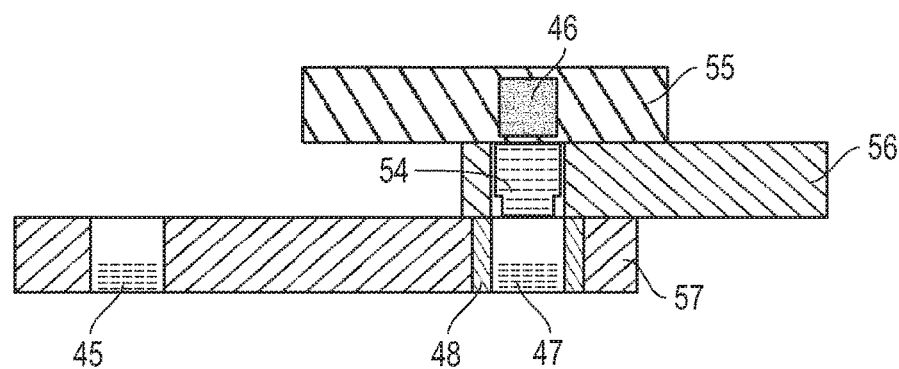

An alternative embodiment whereby disks are replaced with bars and horizontally translated along their long axis can be seen in FIGS. 14a-14c. In FIG. 14a, 3 bars are stacked on top 55, middle 56, and bottom 57. A ferrous block 54 in a cavity in bar 54 was gravity fed into reagent 45. Molecular probes can be deposed to block 54, on the side that enters the reagent. After a suitable incubation period, bar 55 is horizontally translated to align magnet 46 with block 54, and to use magnetic forces to lift the block 54 out of reagent 45 (FIG. 14b). Bars 55 and 56 are horizontally translated to position the block 54 (and constituents bound to the probes) over reagent 47 (FIG. 14c). Bar 55 can be translated to remove the magnetic 46 forces and allow block 54 to be gravity fed into reagent 47 for thermal cycling 48. In certain embodiments, additional capabilities and hardware can be disposed to the disk or in the case of an injected molded disk, overmolded into the disk. Such capabilities and hardware include but are not limited to: batteries to power electronics, electronic slip rings to bring power to the rotating disk, electronic sensors, colorimetric indicators, electronics and electronic assemblies, windows, fiber optics, thermal sensors, and the like.

In one embodiment, a disk stack has gears around the circumference and a gear drive means. Between disks are stops that engage the next disk at a specific time much like the mechanism of a combination lock. Gears and stops are arranged such that there is only one drive means for rotation. Rotation and stopping at specific points defines a specific processing sequence. The present disclosed device and method enables sequential processing with only one drive device, for example a motor. One drive device significantly reduces the cost. Combination of gears and stops is contemplated to achieve specific sequences and capabilities. One embodied capability is rotating a disk at the centrifugation speeds required for processing. In an alternate embodiment, each disk is driven separately by a drive device. The disk circumference or the annular axis can be geared, or both, and they can be driven by gear devices. Motors can be stacked to reduce space, and hollow shafts can be employed, independently driving each disk. In a storage and disposal embodiment, the disks are stored in a metallized plastic Ziploc container that is sealed in addition to the Ziploc. The packaging mitigates oxygen, light, and moisture, and provides for a Ziploc means for disposal. In a multi-mode embodiment, the disks have cavities that contain PCR probes and antibody probes for PCR and ELISA assays on the same set of disks. In another embodiment, the disks are used to detect pathogens such as viruses and bacteria. Detection devices for toxins and proteins are know in the art and can be adapted to the disks of the present disclosed invention. In another embodiment, the disks can be adapted to other detection devices and wireless devices to be dropped from the air into areas of interest and automated to transmit their findings.

Figure 15:
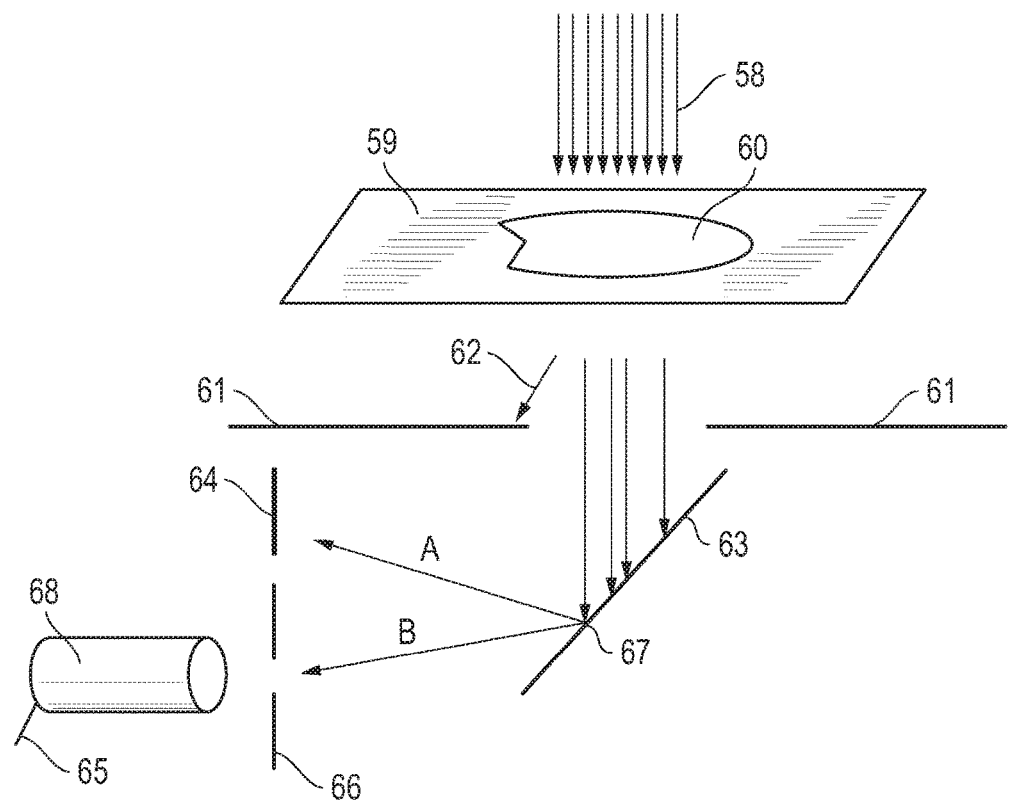
FIG. 15 is an illustration of an electro-optical implementation of the non-optical microscope, according to an embodiment of the present invention.

FIG. 15 is a schematized illustration of an embodiment wherein an electro-optical element is utilized to redirect a one-pixel ray bundle to a pinhole for spatial subsampling. In FIG. 15 a collimated light source 58 is directed toward a microscope slide 59, which has a blood sample 60 on the surface. Rays from the ray bundle 58 pass through the sample 60, are absorbed by the sample or scattered by refractive differences in the sample or scattering constituents in the sample. Scattered rays 62 are blocked by an aperture 61. Rays that are not absorbed or scattered impinge upon an electro-optical device 63 such as a Texas Instrument Digital Mirror Device (DMD). The DMD is divided into digitally controlled elements or mirrors that reflect light in predetermined angles. Each mirror is herein referred to as a pixel. A pixel 67 can reflect light at two different angles A and B. If a pixel 67 is set to reflect light at angle A, a ray bundle the size of the pixel 67 would be directed to an aperture stop 64. If a pixel 67 is set to reflect light at an angle B, a ray bundle the size of the pixel 67 would be directed to a spatial sub-sampling pinhole 66 in front of a detector means 68. The pinhole 66 is smaller than the pixel ray bundle, and can be as small as one-quarter the wavelength of light in the ray bundle. Spatial sub-sampling occurs when the pinhole 66 is translated through the pixel ray bundle and samples are electronically collected 65 by detector means 68. The pinhole can be translated through the pixel ray bundle, by for example, raster scanning means or spinning disk means both know in the art. At each sub-sampling point, an electronic signal is stored that represents the light flux at that point. Raster scanned signals can be organized by the order, row and column that they were collected and displayed to form an image of the light impinging upon the pixel, and therefore an image of the blood sample. For an image of the entire blood sample, a DMD array would be used and one pixel at a time directed for sub-sampling until all the pixels in the array are sub-sampled. The pixels would then be organized by the order, row and column that they were collected and displayed to form an image of the entire blood sample. For example, if a pixel was sub-sampled using a 10×10 grid pattern, then 100 sub-samples (10*10) would be organized to form a pixel level image of the blood sample. If the DMD array was a 20×20 element array, then there would be 400 pixels (20*20). Each pixel has 100 sub-samples and there are 400 pixels; then an image of the blood sample would be comprised of 40,000 samples (100*400) organized in a 200×200 array. Therefore, the pinhole size, spacing of the sub-sampling points, and the number of sub-samples together determine the image resolution. The size of the DMD array determines the field-of-view.

The digital image derived by one embodiment present invention can be stored on any digital media. The simplicity of the present invention provides for a very low cost, fast, high resolution microscope that can be housed in a small form factor such as a compact disk player form factor—and inserted into a personal computer compact disk bay. In one embodiment, light is from an LED light source; other light sources can be used such as different color LEDs blended together to form a composite color, tungsten filament, halogen, xenon, and the like know in the art. The light is directed through a microscope slide that has a sample of blood on the surface. Rays from the light can be collimated or angled as long as the orientation is generally known. After passing through the sample, the light impinges upon a DMD or other electro-optical means that can include Lcos, PDP, mirrors, and the like known in the art. The DMD modulates individual pixels to redirect the light to a detector means. Preferably, the detector is a PMT which affords several decades more of noise free dynamic range as compared to photo diode or charge coupled based devices, but can be any electronic means including avalanche detector, photo diode detector, infrared detector, charge-coupled detector, and the like known in the art. In the light path between the DMD and detector means is placed a means for spatial sub-sampling. Spatial sub-sampling means includes pinholes, spinning disks, and the like know in the art. Thus, the light source, electro-optical modulator, detector means and pinhole for sub-sampling, become a simple assembly that can fit in a small housing many fold smaller than an optical microscope with comparable capabilities, and for a lower cost-to-manufacture.

Sub-sampling is a technique used to improve resolution wherein samples of the whole are taken in smaller increments. One common implementation is to sample a subset of the whole using a pinhole; other implementations can include different shaped holes, variation of coaxial aligned apertures, spinning disks, and the like known in the art. There are many combinations and implementations know in the art. In one embodiment, the pinhole size is approximately equivalent to one-quarter the size of the shortest wavelength of light used for illumination. The pinhole is translated through the ray bundle and sub-samples of the whole are collected as digital signals. There are many suitable translation means; piezo electric, piezo motors, motorized translation stages, spinning disks, and the like know in the art. Sub-samplers can be purchased commercially and are used in optical confocal microscopes such as Zeiss. For example, if a 360 nm light source were used, than the pinhole would be approximate 90 nm or one quarter of 360 nm. In this example, the resolution achieved would be approximately 90 nm as is know in the art. Other resolutions are contemplated using different wavelengths of light and sampling strategies.

In the embodiment wherein the Texas Instrument DMD is used, additional capabilities are added. The Texas Instrument DMD electro-optically modulates light by redirecting the reflection to one of three positions in space; positions 1-3. The first position is a neutral position. In one embodiment, an imaging device is placed at the position 1. In this case light directed from the DMD to the imaging device would have, at best, the resolution of the imaging device's pixel size. A sub-sampled detector assembly could be at position 2, and a second sub-sampled detector assembly could be at position 3. It is contemplated that one or more positions could be configured to collect fluorescent light in a manner know in the art.

In an alternate embodiment requiring precisions alignment, a matched aperture and spatial sub-sampling means are used to replace electro-optical elements. In one example, an aperture and pinhole are aligned such that the aperture receives a ray bundle that has passed through the sample. The aperture blocks ray elements that are malaligned after passing through the sample, thus the aperture allows for the passage of a ray bundle with substantially aligned ray elements. In line with the ray bundle exiting the aperture, is a pinhole for spatially sub-sampling that bundle. Three parameters can be adjusted to control for resolution and image quality; aperture size, aperture to pinhole distance, and pinhole size. In general, the smaller the pinhole and aperture size along with the larger the distance or gap between the aperture and pinhole, the better the image quality. Each can be optimized with undue experimentation starting with an aperture size equal to twice the average illumination wavelength, an aperture-to-pinhole gap of 25 mm and a pinhole size equal to the average illumination wavelength.

In an embodiment of a system for collecting and storing images for diagnostic and prognostic analysis from a data base of images; microscope slides containing a sample, such as a patient's tissue, are imaged using the non-optical microscope and the image stored in a database as is known in the art. The database can be mined for information about slides in general, about slides matching selection criteria, and/or inquiries made about specific slides. This is a novel system in that images collected by the non-optical microscope of the present invention have unique image qualities not seen with conventional optical collections i.e., different dynamic range, depth of field, color range, resolution, and the like. The data mining processing is unique since it depends upon the unique image characteristics. An example would be to sort the images based upon one or more decades of dynamic range—an example of unique data processing enabled by the system. Therefore, the collected image database will provide unique insights that will improve understanding and can be data mined for improved healthcare or a better scientific understanding or, crossed mined with other databases. While illustrations and examples are provided to enhance the understanding of the present invention, other embodiments are contemplated. Pinhole translation for spatial sub-sampling is one implementation for ray bundle sub-sampling. An alternative would be to fix the position of the pinhole and translate the microscope slide. In several examples a microscope slide is used as the sample carrier because it is easily understood. However, there are numerous solid phase sample carriers that can be used that are know in the art. The present invention can be modified for epi-illumination and collection utilizing an x-cube, polarizing cube, dichroic cube, filter, mirror, angling or other means know in the art to separate the illumination light from the light exiting the sample. Optical elements can be added anywhere in the light path to modify the ray bundles without deviating from the spirit of the invention.

Figure 16:
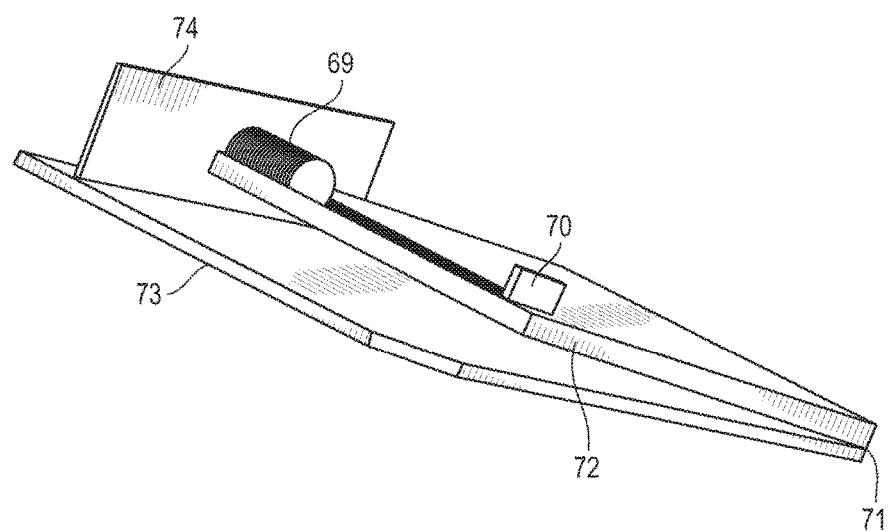
FIG. 16 is an illustration of a horizontal objective on a hinged translation means, according to an embodiment of the present invention.

According to one embodiment of the present invention, in a digital microscope that fits into a CD form factor embodiment, a hinged stage with a microscope objective horizontally disposed to the stage is contemplated. FIG. 16 illustrates an arraignment that enables both 1) the use of conventional microscope objectives and 2) a digital microscope size reduction that will fit in a CD bay envelope. One of ordinary skill in the art will appreciate the simplicity and cost savings. A microscope slide 74 is translated in the long axis of the microscope slide 74 in a plane parallel to the plane of the first element of the microscope objective 69 by conventional means. The microscope objective 69 is disposed to a hinge element 72; having a hinge or pivoting point 71 with a second hinge element 73. In one embodiment, the second hinge element 73 serves as the base plate for the CD bay digital microscope. The first hinge element has the objective 69 disposed to it, and can have a camera 70 for receiving the image from the objective 69. The image path between the objective 69 and the camera 70 can be folded, and other cameras can be added to the path for additional features. Those features can include, but are not limited to, fluorescence, three color or multicolor image collection, confocal imaging, auto focusing elements, and the like. In addition to the hinge simplifying and reducing the cost of translation (by translating the objective along a radii), and reducing the overall size; the hinging point can serve as a focusing or z translation axis. For example, the annular axis of the objective 69 is co-aligned with the annular axis of hinge 71. Thus any translations along the annular axis of the hinge is the same as a focusing the objective 69. When the digital microscope is place in the PC the base plate 73 is a horizontal plane and the second hinge element 72 translates radially up and down, moving the objective and aligned camera across the sample on the microscope slide 74. Focusing is accomplished by moving the hinge element 72 toward the slide or away from the slide (along the annular axis of the hinge). According to an embodiment of the present invention, this is a digital microscope with a focus and translation axis that utilize the same hinge means i.e., two movement directions that are perpendicular to one another. There are piezo-electric means know in the art for controlling focusing movement, and is preferred for precise control over sub-micron movements.

In an alternative embodiment, the unit (FIG. 16) is rotated such that the slide 74 is parallel to the ground and second hinge element 72 is above it and perpendicular to the ground.

Figure 17:
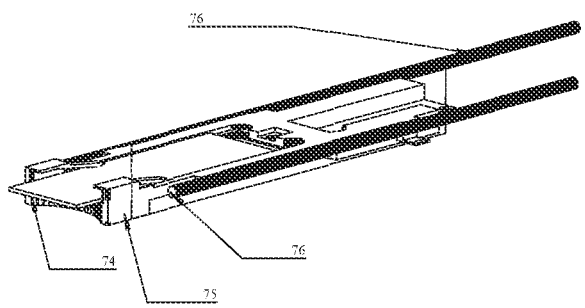
FIG. 17 is an image the slide holder with translation means, according to an embodiment of the present invention.
Figure 18:
FIG. 18 is an image of a system with a vertical objective on a hinged translation means, according to an embodiment of the present invention.

In the embodiment of FIG. 17 images are acquired along an arc (hinge element 72 moves through an arc). As images are collected along the arc, pixels in the camera sensor rotate. Consequently, unless the sensor is in the exact same arc position no two pixels will have the same rotation the result is that no two pixel images will be the same. The pixel rotation leads to aberrant imaging in juxtaposition pixels collected with different arc angles. The instant invention is a method to induce aberrancy in juxtapositioned pixels utilizing an image collection from an arced image collection path. In addition, stitching said aberrant images yields the instant invention of deterministic aberrancy utilizing images collected from an arced image collection path.

In an additional embodiment (FIG. 16), the illumination source is below the slide 74 such that the illumination's annular axis is in substantially the same annular axis as the objective, thereby providing illumination through the slide, through the objective and to the camera. Said illumination source is disposed to the hinge element 72 and thereby moves in synch with the radial movement of the objective. Furthermore, by being disposed to the hinge element 72, as the objective moves to up and down for focusing the illumination source remains at a fixed distance from the objective. This is a unique feature whereby the illumination source, the objective, and the camera are moved together during focusing. Said source can consist of a laser, LED, incandescent, quantum source, or other illumination sources known in the art. Thus, hinge element 72 controls 4 features: image focus, an imaging axis, the illumination focus, and the illumination axis. Said illumination has a NA approximate equivalent to the imaging optics and optical path length of less than 7 cm. In the instant invention, the LED dome, 2 aspherical lens, an achromatic lens and a mirror comprise the optical assembly; and having an optical path of less than 7 cm. The LED dome is utilized as an optical element. All lens diameters are less than 15 mm; the exiting light focal distance is less than 5 mm. Lens are commercially available and spacing is adjusted depending on the NA requirements as is known in the art.

In an embodiment for repositioning the objective 69 in a deterministic manner at power down (FIG. 16), a spring is disposed to the hinge element 72 and in the annular alignment of the axis such that the least tension position moves the hinge element 72 containing the objective 69 away from the slide. For example, if hinge element 72 is in a vertical position and power turns off the objective 69 will not be forced into the slide 74 by gravity but be moved away from the slide by the spring. A spring can refer to a coiled structure, a memory shaped structure, or other tension positioning structures known in the art.

In an embodiment for moving a slide 74 along an axis for microscopy (FIG. 17), a slide 74 is held by means of a slide holder 75. Said slide holder 75 is disposed between two rods 76 that are parallel to each other. The slide holder 75 has a v-notch or other configurations known in the art that aligns and suspends the slide holder 75 between the rods 76. The rods 76 may be iron, stainless steel, tungsten carbide or other metals known in the art. Preferably, the rods 76 are polished tungsten carbide. The slide holder 75 can be any material; preferably the slide holder 75 is comprised of a composite plastic. Said composite may include ceramic, grapheme, carbon, glass, aluminum, or other materials known in the art. In the embodiment there will be friction between the slide holder 75 and the rods 76. Said friction will be reduced by said composite material. Moreover, as the plastic wears away more composite material is exposed further reducing friction and establishes a better fit between the slide holder 75 and the rod 76. This method of movement is used for sub-wavelength limit microscopy, wavelength limit microscopy, and supra-wavelength microscope; including fluorescence, confocal, multi-photon, and other microscopy means known in the art.

In an alternative embodiment, the microscope is comprised of composite plastic. Said composite may include ceramic, grapheme, carbon, glass, aluminum, or other materials known in the art. While composite plastids do not provide the same rigidity, stability, strength, and durability that metals provide for wavelength limited microscopes, the lack of rigidity, stability, strength, and durability are compensated in software by having the microscope recalibrate itself upon slide 74 insertions. The instant invention is a composite microscope that is capable of wavelength resolution.

An alternative embodiment is an illumination system utilizing an illumination source of individual colors that is fixed in position relative to the objective as previously described. The imaging camera is monochromatic. The colors are turned on individually or in groups and an image collected. Specific colors can be turned on to create specific effects: For example a red image, green image and a blue image can be combined into a color image by algorithms known in the art. Infrared can be combined with green images to highlight specific refractive angles.

In one embodiment of the present invention, focusing movement is accomplished using a stepper motor and cam shaft. In the most cost effective embodiment, a bearing is pressed on to a stepper motor shaft with a 1 mm offset from the annular axis of the shaft. The offset will displace whatever the bearing is positioned against by 1 mm as it rotates one revolution. If a stepper motor is used that has 200 steps per revolution then the 1 mm displacement can be divided into 100 discrete increments (100 up then 100 down). How to calculate the step distances is know in the art. Utilizing a micro stepping driving means for the stepper motor can further reduce the discrete steps into sub-micron increments—important in high resolution microscopy where the depth of field is less than one micron. Beyond the cost advantage, the cam stepper motor focusing invention is faster and can move significantly more weight. The enhanced focusing capabilities, weight and speed, enable focusing by moving the entire hinge element 72 instead of just the objective. In one embodiment a stepper motor is disposed to the hinge element 72 and the bearing in contact with hinge element 73. As the stepper motor rotates, the hinge element 72 is displaced from hinge element 73 by 1 mm. Consequently, the microscope objective 69 will move closer or further from the microscope slide over a 1 mm span. The microscope objective 69 is positioned such that a sample on the microscope slide 74 comes into focus within that 1 mm span. In an alternate embodiment, a motor shaft with an offset center provides a cam shaft motion for focusing. Said cam motion is sinusoidal having finer movements at peak and troughs. Setting the finer movement at or near where the objective focuses on the sample yields finer focal positioning with each motor step. The instant invention enables sub-nanometer positioning.

In an alternate compact embodiment, a microscope slide is translated in x y and z directions by magnetic levitation and position sensors. In one embodiment a microscope slide holder with magnets disposed around the periphery is used for translation. The slide holder is placed in a surrounding housing having magnets oriented so that their magnetic fields opposes those disposed to the slide holder; both field sets balanced in such a way as to suspend the holder without contacting the enclosure. Also in the surrounding housing is a set of electromagnets of lesser field density (for cost and power reduction) and position sensors as is known in the art. The preferred sensor is a laser diode interferometer for node counting. Magnetic field density for the electromagnetic are adjusted to mitigate or augment the fixed magnetic fields from the housing magnets. In doing so, gravity will move the slide in a predictable direction—x y or z. Once the position sensors have detected that the slide holder has reached the predetermined coordinate, the electromagnets will be adjusted to hold the slide holder in that position. The negation or augmentation of a fixed magnetic field reduces size and cost, and simplifies the control.

The microscope slide is a diagnostic vehicle used to attach indicators to determine concentrations of various substances. It is also use as a vehicle to support the imaging of, for example, blood and other body fluid constituents. The disk stack embodiment is another diagnostics vehicle for analyte analysis and imaging, and adds the ability to process samples. In general, a diagnostics vehicle is herein defined as a support structure that is used by the digital microscope to physically hold or hold and process samples. The microscope slide may be mirrored on the side contiguous with the sample for an improved signal-to-noise ratio in epi-illumination.

In an embodiment for 3-dimensional imaging of a sample on a microscope slide, the objective z axis (focal axis) is moved up and down in a sine wave pattern. Said sine wave zero point is the focal point of the objective. Said zero point is positioned for optimal resolution of a portion of the sample on the microscope slide. While the z axis is oscillating in a sine wave function, there is linear movement along one or both of the other axes. Images are collected during oscillations and linear movement. The period of said sine wave oscillation is substantially equal to the field of view whereby one oscillation period is complete in the time it takes to linearly move a distance substantially equal to the field of view seen by the imaging camera. Overlapping in and out-of-focus images are collected and deconvolved by methods known in the art, and converted into a 3-dimensional representation for display by methods known in the art. Hence a method for collecting images from a microscope slide by moving in a specific pattern that yields images useful for 3-dimensional image reconstruction.

The current art moves a sample to a location determined by the operator or to a location somewhere in a sample. In a grid invention embodiment, a coordinate grid is mapped to the imaging area. The grid spacing is less than or equal to the field of view size of the imaging device. For example the combination of a high magnification microscope objective and camera may yield a 100 micron square field of view. The grid size would be 100 microns×100 microns, or less. The lesser amount would enable pixel overlap between images or frames and that overlap could be used for stitching and/or blending as previously described and known in the art. Instead of the current art whereby an image is obtained at some location, in the current invention images are obtained at the intersecting points that form the grid. Thus, when an operator points to a location that is not a grid intersection, instead of going to the operator instructed location, the image is collected at the grid intersection that is closest to the operator instructed location. If, for example, the next operator instructed location is three pixels away from the first location, the next image is not taken at that location but is taken at the nearest grid intersection that does not include the first intersection taken. Consequently, there are several efficiencies obtained through the use of this method: fewer images are taken for small displacements, the coordinate for every image is apriori, fixed and known, and the pixel overlap is fixed—resulting in faster and better image stitching.

An expanded field of view invention utilizes the grid previously described and has an automated feature. In expanded field of view, an image is taken at a grid point nearest to a chosen location, then images are automatically collected at each of the grid points that surround the first grid point. For example, a single image is taken at a grid point followed by images automatically collected at the surround eight grid points. Said nines images are stitched or tiled together to form a larger image, hence a larger field of view.

At high frame rates, images could be collected and stitched or tiled together, and give the perception that the field of view was larger. Moreover, efficiency is improved because contiguous frames are typically in focus and therefore do not require additional focusing frames. Furthermore, since the larger field of view typically has more pixels that can be displayed, the image can be zoomed out thereby providing more contextual information. Thus, in an additional embodiment, single point areas of interested are collected along with contiguous contextual information from the surrounding images; all of which is stored. Instead of storing entire scanned slides, just the areas of interested are stored along with the surrounding contiguous context. The invention herein referred to a contextual point data. Point data on a grid can range from a single grid point to many grid points. Contextual data can include a single frame collection that surrounds all the points to several frames concentrically radiation out from the center point collection. These features can be preset by the end user.

In an alternate embodiment, the digital microscope of this invention is connected to a cell phone for power and or communications. For example, the digital microscope of this invention can be operated and powered by a cell phone using standard USB power and connectivity.

In an alternate embodiment, the slide used for sample holding can be replaced with a biochip or biodisk as is known in the art. Imaging at wavelength limit resolution is enabled as is the capability to image at different locations. Single point imaging can be obtained thereby forgoing the need for xy motion control; just using wavelength limit imaging and focusing.

A method for clinical diagnosis using both morphological and assay metrics on the same sample and having a sample analysis volume of less than 79 ul comprising; an automated microscope having wavelength limit resolution and a slide with diagnostic microarray assays disposed to the slide as is known in the art, and disposed in a proximity that will be in contact with a 79 ul droplet that has been dispersed onto the slide. An automated microscope is defined as a microscope that has x, y, and z axes controlled by software (or just z axis), has autofocus software, and is at least partially built with composite plastics. An assay metric may consist of at least one of: colorimetric, fluorometric, immunoassay, genetic assay, nanoparticles assay, or others that are known in the art and may asses constituents that include: parasites, malaria, proteins, chemicals, dissolved gas, bacteria, virus, intracellular structures, spores, DNA, RNA, or other constituents known in the art. Said sample may include; whole blood, tissue, sputum, feces, sweat, tissue exudates, urine, serum, or other sources known in the art. Said slide is a mechanical structure adapted to accommodate a sample and diagnostic microarray, and adapted to be used for clinical related diagnostics in an automated microscope.

A slide for clinical diagnostics comprised of a mechanical carrier upon which diagnostics assays are disposed, the diagnostic assays are in an area that receives a sample, a portion of said area being transparent and having a surface finish of less than 40 micro-inches RMS, and said slide adapted to be received by an automated microscope.

It is clear that at-home diagnosis, testing, and medical record maintenance is a departure from convention. It will be recognized by those skilled in the art that changes may be made to the above-described embodiments of the invention without departing from the broad inventive concepts thereof. It is understood therefore, that this invention is not limited to the particular embodiment disclosed, but is intended to cover any modifications that are within the scope and spirit of the invention as defined by the appended claims.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

I claim:

1. A doctorless business method for self-collection of whole blood diagnostic information comprising:
   a digital microscope having x, y, and z axes automated movement means and wavelength limited resolution,
   said movement means moving a self-collected whole blood specimen, that is imaged by said digital microscope,
   said digital microscope collecting images directly from a camera chip that is an attached and integrated into said digital microscope,
   wherein said camera is not an iPhone camera,
   said images being of whole blood nuclei and constituents from said specimen,
   said image data from said collected images, processed to identify said nuclei and constituents,
   the diagnostic information from said processing of said image data provided to said specimen donor, and
   said specimen donor is not a physician.

2. A doctorless business method for self-collection of whole blood diagnostic information comprising:
   a digital microscope having x, y, and z axes automated movement means and wavelength limited resolution,
   said movement means moving a self-collected whole blood specimen, that is imaged by said digital microscope,
   said digital microscope collecting images directly from a camera that is an attached and integrated into said digital microscope,
   wherein said camera is not an iPhone camera,
   said images being of whole blood nuclei and constituents from said specimen,
   said image data from said collected images, processed to identify said nuclei and constituents, the diagnostic information from said processing of said
   image data provided to said specimen donor,
said specimen donor is not a physician, and
billing for said information.

* * * * *